US005763160A

United States Patent [19]

Wang

[11] Patent Number: 5,763,160

[45] Date of Patent: Jun. 9, 1998

[54] SYNTHETIC PEPTIDES AND PROCESS OF USING SAME FOR THE DETECTION OF ANTIBODIES TO HUMAN IMMUNODEFICIENCY VIRUS (HIV) GP120 ENVELOPE PROTEIN, DIAGNOSIS OF AIDS AND PRE-AIDS CONDITIONS AND AS VACCINES

[75] Inventor: Chang Yi Wang, Greak Neck, N.Y.

[73] Assignee: United Biomedical, Inc., Hauppauge, N.Y.

[21] Appl. No.: 488,252

[22] Filed: Jun. 7, 1995

Related U.S. Application Data

[62] Division of Ser. No. 326,676, Oct. 19, 1994, abandoned, which is a continuation of Ser. No. 726,605, Jul. 9, 1991, abandoned, which is a continuation-in-part of Ser. No. 663,262, Mar. 1, 1991, abandoned, which is a division of Ser. No. 155,321, Feb. 12, 1988, abandoned.

[51] Int. Cl.[6] .......... C12Q 1/70; G01N 33/569; C07K 14/16; A61K 39/21

[52] U.S. Cl. .......... 435/5; 435/7.1; 435/69.3; 530/300; 530/324

[58] Field of Search .......... 435/5, 7.1, 69.3; 530/300, 324

[56] References Cited

U.S. PATENT DOCUMENTS

| | | | |
|---|---|---|---|
| 4,629,783 | 12/1986 | Cosand | 435/5 |
| 4,956,273 | 9/1990 | Kennedy et al. | 435/5 |
| 5,017,688 | 5/1991 | Gilbert et al. | 435/5 |
| 5,019,387 | 5/1991 | Haynes et al. | 435/5 |
| 5,166,050 | 11/1992 | Shriver | 435/5 |
| 5,229,490 | 7/1993 | Tam | 530/324 |

FOREIGN PATENT DOCUMENTS

| | | |
|---|---|---|
| 199301 | 10/1986 | European Pat. Off. . |
| 255190 | 2/1988 | European Pat. Off. . |
| 273716 | 7/1988 | European Pat. Off. . |
| 306219 | 3/1989 | European Pat. Off. . |
| 311219 | 4/1989 | European Pat. Off. . |
| 311228 | 4/1989 | European Pat. Off. . |
| WO8602383 | 4/1986 | WIPO . |
| WO8702038 | 4/1987 | WIPO . |
| WO 8702775 | 5/1987 | WIPO . |
| WO8707616 | 12/1987 | WIPO . |
| WO8800471 | 1/1988 | WIPO . |
| WO8809181 | 12/1988 | WIPO . |
| WO8905821 | 6/1989 | WIPO . |
| WO 8907112 | 8/1989 | WIPO . |
| WO9003984 | 4/1990 | WIPO . |

OTHER PUBLICATIONS

Encyclopedia of Polymer Science and Engineering, second edition vol. 12 p. 398, Jan. 1, 1988.
DeVita et al. AIDS: Biology, Diagnosis, Treatment and Prevention. 4th ed. Lippincot-Raven Pub. Jan. 1, 1997.
Chang, T.W. et al. *Biotechnology*, 3, 905–909 (1985).
Wang, J.J.G. et al. *Proc. Natl. Acad. Sci. USA*, 83, 6159–6163 (1986).
Matthews, T.J. et al. Proc. Natl. Acad. Sci. USA, 83, 9709–9713 (1986).
Homsy, J. et al. Immunology Today, 8, 193–196 (1987).
Rusche, J.R. et al. *Proc. Natl. Acad. Sci. USA*, 84, 6924–6928 (1986).
Lasky, L.A. et al. *Science*, 233, 209–212 (1986).
Barr, P.J. et al., *Vaccine*, 5, 90 (1987).
Putney, S.D. et al. *Science*, 234, 1392–1395 (1986).
Dalgleish, A.G. et al. *Nature* (London), 312, 763–768 (1984).
McDougal, J.S. et al. J. Immunol., 135, 3151–3157 (1985).
Cease, K.B. et al. *Proc. Natl. Acad. Sci. USA*, 84, 4249–4253 (1987).
Pert, C.B. et al. *Proc. Natl. Acad. Sci. USA*, 83, 9254–9258 (1986).
Chanh, T.C. et al. *EMBO*, 5, 3065–3071 (1986).
Chanh, T.C. et al. *Eur. J. Immunol.*, 16, 1465–1468 (1986).
Merrifield, R.B. *J.A.C.S.*, 85, 2149–2154 (1963).
Prince, A.M. et al. *J. of Infectious Diseases*, 156, No. 2, 268–272 (1987).
Tam, J. P. and Zavala F., *J. Immunol, Methods* 124: 53–61 (1989).
Robey, W.G. et al. *Proc. Natl. Acad. Sci. USA*, 83, 7023–7027 (1986).
Palker, T.J. et al. *Proc. Natl. Acad. Sci. USA*, 84, 2479–2483 (1987).
M.S. application Ser. No. 07/121,464, Nov. 17, 1987 H. T. Kao.

*Primary Examiner*—Marian C. Knode
*Assistant Examiner*—M. K. Zeman
*Attorney, Agent, or Firm*—Morgan & Finnegan,LLP

[57] ABSTRACT

This invention relates to a method using synthetic peptides as the solid phase immunoadsorbent for the detection and elicitation of antibodies to Human Immunodeficiency Virus (HIV) gp120, and, in particular, antibodies having HIV neutralizing capabilities. The amino acid sequences of the peptides correspond to segments of the external envelope protein gp120 of HIV. These peptides have been found to be highly immunogenic, and are reactive with antibodies in sera of patients with AIDS, ARC or HIV infected individuals. They can also be used to elicit the production of neutralizing antibodies to HIV. More specifically, the present invention is directed to the use of a synthetic peptide selected from the groups consisting of peptides containing thirty-three amino acids in a prescribed sequence derived from the HIV-gp120 external protein, analogues, mixtures and poly-L-lysine polymers thereof, for the detection and elicitation of antibodies to HIV-gp120. It is particularly useful for the detection and elicitation of antibodies having HIV neutralizing capabilities. The detection method includes an enzyme linked immunoassay and other forms of immunoassay procedures. The present invention also relates to a method for generating high titer neutralizing antibodies to HIV gp120 protein in healthy mammals, including humans, by the use of the synthetic peptides, their analogues or mixtures in either a conjugated or a polymeric form as a key component in a synthetic vaccine for the prevention of AIDS.

23 Claims, 11 Drawing Sheets

SYNTHETIC PEPTIDES AND PROCESS OF USING SAME FOR THE DETECTION OF ANTIBODIES TO HUMAN IMMUNODEFICIENCY VIRUS (HIV) GP120 ENVELOPE PROTEIN, DIAGNOSIS OF AIDS AND PRE-AIDS CONDITIONS AND AS VACCINES

CROSS REFERENCE TO RELATED APPLICATIONS

This is a divisional application of application Ser. No. 08/326,676 filed Oct. 19, 1994, now abandoned, which in turn is a continuation of application Ser. No. 07/726,605 filed Jul. 9, 1991, now abandoned, which is in turn a continuation-in-part application of application Ser. No. 663,262, filed Mar. 1, 1991; now abandoned which is a divisional application of application Ser. No. 155,321, filed Feb. 12, 1988, now abandoned.

INTRODUCTION

This invention relates to a method using synthetic peptides for the detection of antibodies to Human Immunodeficiency Virus (HIV) gp120, in particular, antibodies having HIV neutralizing capabilities and as vaccines. The amino acid sequences of the peptides correspond to segments of the external envelope protein gp120 of HIV. These peptides have been found to be highly immunogenic, and are reactive with antibodies in sera of patients with AIDS, ARC, or HIV infection. They can also be used to elicit the production of neutralizing antibodies to HIV. More specifically, the present invention is directed to the use of a synthetic peptide selected from the groups consisting of peptides, with from about 15 to 40 amino acids, in a prescribed sequence, their analogues and mixtures, corresponding to a part of the HIV gp120 external protein for the detection and elicitation of antibodies to HIV gp120. It is particularly useful for the detection and elicitation of antibodies having HIV neutralizing capabilities. The detection method includes an enzyme linked immunoassay and other forms of immunoassay procedures. The present invention also relates to a method for generating high titer antibodies to HIV gp120 protein in healthy mammals, including humans, by the use of the synthetic peptides, in either a conjugated or a polymeric form, and analogues or mixtures thereof as the key component in a synthetic vaccine for the prevention of AIDS.

BACKGROUND OF THE INVENTION

Since the human immunodeficiency virus (HIV) started its spread through the human population, the AIDS epidemic has steadily increased worldwide for the lack of any therapeutic or preventive means for intervention. The unique pathogenicity and the variability of HIV have raised new challenges in the design, testing and evaluation of therapeutics and vaccines for HIV. It appears, for the moment, that the development of an effective method for the detection of HIV infection and an effective vaccine remain the only means by which the disease is to be controlled and eradicated.

An ideal vaccine against HIV infection should be highly immunogenic, induce both T and B cell mediated virus-specific immunity, and be free of irrelevant carrier proteins. Although traditional approaches using whole virus or viral protein subunits can generally achieve this goal, practical considerations, such as the safety and availability of native antigen, have led many to consider other highly engineered vaccine constructs for AIDS.

Studies on the feasibility of a virion subunit vaccine to protect against viral infection have mainly focused on the envelope protein of the HIV, the precursor gp160 protein and its derived external protein, gp120, and the transmembrane protein, gp41.

The transmembrane protein gp41 of HIV has been found to be highly antigenic in that upon infection, all individuals develop antibodies to gp41 which have been detected by recombinant proteins containing segments of gp41 (1) or by this synthetic peptides covering a well defined region of this protein (2).

It is well documented that HIV infected subjects make antibodies to gp120 (3). However, the immunogenic sites and their corresponding amino acid sequences on this molecule have not yet been identified.

A recent article reported the status of the intense efforts directed to the finding of a suitable candidate for a vaccine (4). These efforts are mainly directed to the use of the external portion of the HIV envelope glycoprotein, gp120. Native gp120 was purified from HIV producing cell lines but gave very low yields (3). Moreover, although native gp120 showed toxic effect on CD4 positive cells, it only elicited moderate neutralizing antibody titers and failed to elicit antibody-dependent cell mediated cytotoxicity in the studies using chimpanzee hosts (3).

Recombinant proteins that contain the whole envelope protein gp160, the external envelope protein gp120, or portions of gp120 have been produced in insect cells (5), mammalian cells (6), yeast cells (7), and in *Escherichia Coli* (8). Purified gp120 has also been shown to bind the cell receptor CD4 (9,10), and to elicit neutralizing antibodies from immunized animals (11). Reports employing synthetic peptides representing small segments of gp120 have revealed various regions to be immunoreactive, these include two modest antigenic regions as being reactive to sera from a few HIV infected patients (12,13), and two regions as representative of helper T cell antigenic sites (14), one region which inhibits HIV receptor binding and T cell infectivity (15), and one region which elicits marginal neutralizing antibodies (16,17).

Pert et al. reported that an 8mer peptide, namely peptide T, as having the ability to inhibit the binding of I-125 labelled HIV gp120 to T4 antigen in brain membranes and block HIV infection of human T cells in vitro (15). Cease et al. reported the identification of an antigenic site of HIV-gp120, represented by a 16mer peptide, named peptide T1, that elicits specifically T cell immunity. However, no results on the peptide's immunoreactivity with serum antibodies derived from HIV infected individuals (i.e. B cell immunity) were reported (14). Palker et al. reported that a 15mer peptide, SP-22, derived from a conserved region at the carboxyl terminus of HIV-gp120, showed moderate immunoreactivity with antibodies of HIV infected individuals. However, these SP-22 peptide reactive anti-gp120 antibodies have clearly been shown to be non-neutralizing (12). Contrary to Palker et al.'s report, Chanh et al. described that a synthetic 30mer peptide, having an overlapping sequence with Palker et al.'s SP-22, showed weak immunogenicity in eliciting neutralizing antibodies to gp120 (16,17). Similarly, Cosand described a peptide conjugate designated as peptide 36-BSA as having moderate antigenic properties with serum antibodies from a few HIV infected individuals (13). Cosand's peptide-36, a 24mer, has an overlapping amino acid sequence with Palker's SP-22 peptide and Chanh's 30mer peptide.

These peptides, their amino acid sequences and reported immunoreactivities are summarized in Table I.

TABLE I

Synthetic HIV gp120 Peptides with Reported Properties

| Peptide Reference | Code | Property | Reference |
|---|---|---|---|
| Val—Lys—Ile—Glu—Pro—Leu—Gly—Val—Ala—Pro—Thr—Lys—Ala—Lys—Arg—Arg—Val—Val—Gln—Arg—Glu—Lys—Arg—Ala (SEQ NO. 31) | Peptide 36-BSA | Moderately antigenic | Cosand, US Patent (13) |
| Ala—Ser—Thr—Thr—Thr—Asn Tyr—Thr (SEQ NO. 32) | Peptide T | Inhibition of HIV infection | Pert et al. (15) |
| Ala—Pro—Thr—Lys—Ala—Lys—Arg—Arg—Val—Val—Gln—Arg—Glu—Lys—Arg (SEQ NO. 33) | SP-22-BSA | Moderately immunogenic, does not react with neutralizing antibodies | Palker et al. (12) |
| Val—Ala—Pro—Thr—Lys—Ala—Lys—Arg—Arg—Val—Val—Gln—Arg—Glu—Lys—Arg—Ala—Val—Gly—Ile—Gly—Ala—Leu—Phe—Leu—Gly—Phe—Leu—Gly—Ala—Gly (SEQ NO. 34) | gp120 503-532 | weakly immunogenic | Chanh et al. (16, 17) |
| Lys—Gln—Ile—Ile—Asn—Met—Trp—Gln—Glu—Val—Gly—Lys—Ala—Met—Tyr—Ala (SEQ NO. 35) | Peptide T1 | Helper T cell antigenic site | Cease et al. (14) |
| His—Glu—Asp—Ile—Ile—Ser—Leu—Trp—Asn—Gln—Ser—Ile—Lys (SEQ NO. 36) | Peptide T2 | Helper T cell antigenic site | Cease et al. (14) |

Our previous attempts in the identification and characterization of highly antigenic epitopes on the gp41 and p24 HIV proteins have made possible the development of an efficacious HIV antibody screening and diagnostic method using synthetic peptides, instead of the virus itself, as the solid immunoadsorbent (2). A similar task in mapping the reactivity of neutralizing antibodies to epitopes on human retroviral protein, in particular the HIV gp120 protein, remains another challenge en route to the design and development of synthetic vaccines for inducing high neutralizing antibody titers and specific cellular immune response to successfully prevent the spread of AIDS.

Neutralizing antibodies (NA) are antibodies that have the ability to neutralize the infectivity of the target virus i.e. to inactivate the virus and/or block its ability to infect susceptible cells. The mechanism of blocking can be at any level of the HIV infectious pathway. Neutralizing epitopes are defined as those epitopes or immunological determinants which elicit a neutralizing antibody response. The capacity of the neutralizing antibody in a serum to inactivate viral infectivity is its neutralizing activity. It is usually expressed as the neutralization antibody titer, an endpoint dilution measured by various bioassay procedures.

One of the bioassays, a quantitative assay, measures the expression of HIV p24 core protein by cells infected with HIV. In this assay, susceptible human tissue culture cells are challenged by infection with a dose of HIV, e.g. 10 times the amount of virus needed to infect 50% of these cells in the absence of antiserum (i.e. 10×50% tissue culture infectious dose, 10×$TCID_{50}$). The infectious dose of virus is pre-incubated with serial dilutions of the test serum which is suspected of containing NA. Each mixture is then used to infect cells. After incubation for two weeks the cells are monitored for viral infection. The end point serum dilution that caused complete inhibition of p24 expression is determined as the neutralization antibody titer. See Table VII and Example 8.

The neutralization antibody titer may also be determined by measuring HIV reverse transcriptase activity generated by the HIV infected and cultured cells. The end point dilution that caused complete inhibition of reverse transcriptase expression is the neutralization antibody titer. See Example 3, Table V and FIG. 3.

Another type of bioassay is a fusion-inhibition assay wherein the ability of virus-neutralizing antibodies to inhibit cell-fusion caused by cell-to-cell transmission of HIV infection is qualitatively determined. In the fusion inhibition assay, cells infected with HIV are mixed with uninfected susceptible cells in the presence of test sera. In the absence of NA, infected cells act as centers of infection, causing uninfected cells to fuse with them and form large multinucleate HIV infected cells called syncytia. The antisera that inhibit this fusion are scored as having fusion inhibition antibodies, see Table VII. Positive results in the fusion inhibition assays could indicate an induction of protective immunity. See Table VII of Example 8.

REFERENCES

1. Chang, T. W. et al. *Biotechnology,* 3, 905–909 (1985)
2. Wang, J. J. G. et al. *Proc. Natl. Acad. Sci. USA,* 83, 9709–9713 (1986)
3. Matthews, T. J. et al. *Proc. Natl. Acad. Sci. USA,* 83, 9709–9713 (1986)
4. Homsy, J. et al. *Immunology Today,* 8, 193–196 (1987)
5. Rusche, J. R. et al. Proc. Natl. Acad. Sci. USA, 84, 6924–6928 (1986)
6. Lasky, L. A. et al. *Science,* 233, 209–212 (1986)
7. Barr, P. J. et al., *Vaccine,* 5, 90 (1987)
8. Putney, S. D. et al. *Science,* 234, 1392–1395 (1986)
9. Dalgleish, A. G. et al. *Nature* (London), 312, 763–768 (1984)
10. McDougal, J. S. et al. *J. Immunol.,* 135, 3151–3157 (1985)
11. Robey, W. G. et al. *Proc. Natl. Acad. Sci. USA,* 83, 7023–7027 (1986)
12. Palker, T. J. et al. *Proc. Natl. Acad. Sci. USA,* 84, 2479–2483 (1986)
13. Cosand, W. U.S. Pat. No. 4,629,783
14. Cease, K. B. et al. *Proc. Natl. Acad. Sci. USA.,* 84, 4249–4253 (1987)
15. Pert, C. B. et al. *Proc. Natl. Acad. Sci. USA* 83, 9254–9258 (1986)
16. Chanh, T. C. et al. *EMBO,* 5, 3065–3071 (1986)
17. Chanh, T. C. et al. *Eur. J. Immunol.,* 16, 1465–1468 (1986)
18. Merrifield, R. B. *J.A.C.S.,* 85, 2149–2154 (1963)
19. Kao, H. T., U.S. application Ser. No. 07/121,464
20. Prince, A. M. et al. *J. of Infectious Diseases,* 156, No. 2, 268–272 (1987)

SUMMARY OF THE INVENTION

The present invention is directed to synthetic peptides having specific immunoreactivity to antibodies to HIV and neutralizing antibodies to HIV gp120, with from about 15 to 40 amino acids, the sequence of which corresponds to regions encoded in HIV gp120 by the HIV env gene, selected from the group consisting of:

(i) Cys-Arg-Ile-Lys-Gln-Ile-Ile-Asn-Met-Trp-Gln-Glu-Val-Gly-Lys-Ala-Met-Tyr-Ala-Pro-Pro-Ile-Ser-Gly-Gln-Ile-Arg-Cys-X Peptide 126 (SEQ NO: 1)

(ii) Gln-Ser-Val-Glu-Ile-Asn-Cys-Thr-Arg-Pro-Asn-Asn-Asn-Thr-Arg-Lys-Ser-Ile-Arg-Ile-Gln-Arg-Gly-Pro-Gly-Arg-Ala-Phe-Val-Thr-Ile-Gly-Lys-X Peptide 127 (SEQ. NO. 11)

(iii) analogues thereof, and (iv) mixtures thereof, wherein X is —OH or —$NH_2$.

The synthetic peptides of the present invention are useful for the detection of antibodies to HIV in physiological fluids and in particular are useful for the detection of neutralizing antibodies to HIV gp120 in physiological fluids.

The peptides of the present invention are also useful as key components in vaccines for the immunization of animals including humans to elicit the production of antibodies to HIV.

BRIEF DESCRIPTION OF THE DRAWINGS

in FIGS. 5*a*–*d*=normal control).

DETAILED DESCRIPTION OF THE INVENTION

Figure 1A:
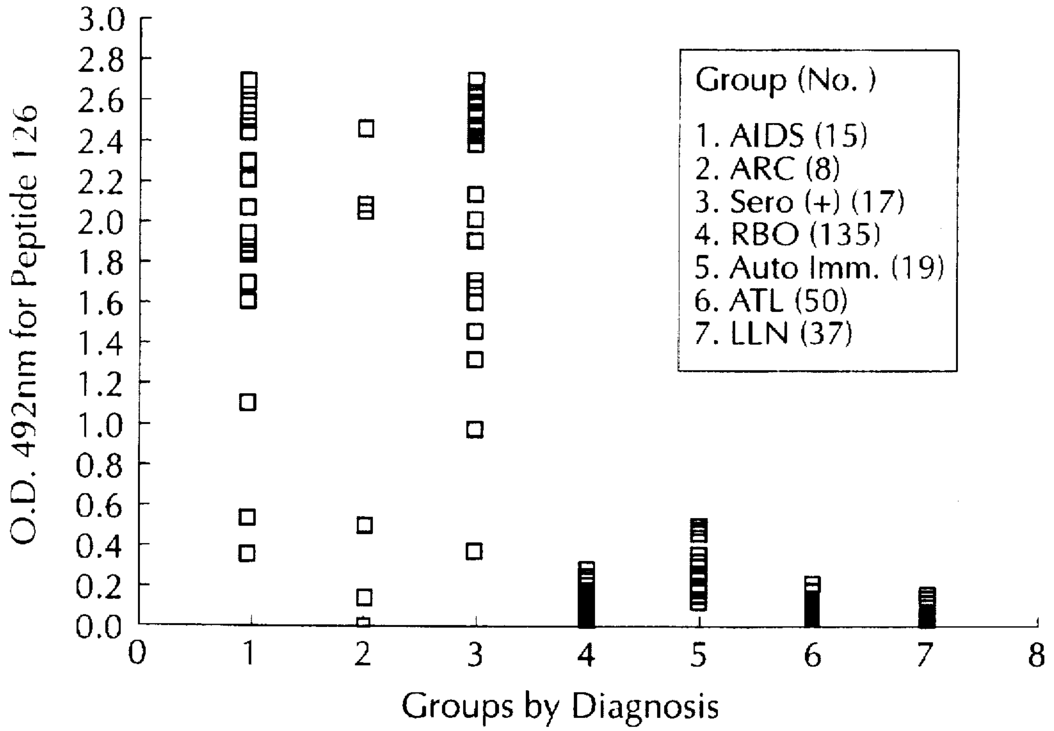
FIGS. 1*a* and 1*b* respectively show the results of EIA assays, using Peptide 126 and Peptide 127 as the solid phase immunoadsorbent, with sera from patients diagnosed to have AIDS, ARC, persons who are known to be seropositive, lymphoid-leukemia malignancies (LLM), autoimmune diseases, adult T-cell leukemia (ATL) and from random blood donors.

The present invention provides novel peptides which immunologically mimic HIV gp120 external envelope protein encoded by the env region of the viral genome.

The peptides have amino acid sequences which correspond to Cys-Arg-Ile-Lys-Gln-Ile-Ile-Asn-Met-Trp-Gln-Glu-Val-Gly-Lys-Ala-Met-Tyr-Ala-Pro-Pro-Ile-Ser-Gly-Gln-Ile-Arg-Cys-X, designated Peptide 126 (SEQ NO: 1), encoded within the bp7053 to bp7136 region of gp120; or Gln-Ser-Val-Glu-Ile-Asn-Cys-Thr-Arg-Pro-Asn-Asn-Asn-Thr-Arg-Lys-Ser-Ile-Arg-Ile-Gln-Arg-Gly-Pro-Gly-Arg-Ala-Phe-Val-Thr-Ile-Gly-Lys-X, designated Peptide 127 (SEQ NO. 11), encoded within the bp6669 to bp6767 region of gp120. The peptides are referred to herein as Peptide 126 and Peptide 127 respectively.

The amino acid sequence of Peptide 126 is taken from a more conserved region in gp120 (Table IIa) whereas the amino acid sequence of Peptide 127 is taken from a highly variable region in gp120 (Tables IIb). Each of the novel peptides show a high level of immunoreactivity with antibodies to HIV and is useful as the immunoadsorbent in a highly sensitive and specific EIA for the detection of antibodies to HIV in body fluids of infected individuals. The EIA results, $A_{492nm}$, obtained by using Peptide 126 or Peptide 127 as the immunoadsorbent also show a high degree of correlation with the neutralization antibody titers of the patients' sera. EIAs using Peptides 126 or Peptide 127 are, therefore, useful for simple and rapid detection of HIV neutralizing antibodies in sera.

As contemplated by the present invention, the peptides having specific immunoreactivity to antibodies to HIV and, in particular, useful for the detection of HIV gp120 neutralizing antibodies comprise peptides having from about fifteen to forty amino acids in a sequence corresponding to regions encoded by HIV gp120 selected from the group consisting of:

(i) Cys-Arg-Ile-Lys-Gln-Ile-Ile-Asn-Met-Trp-Gln-Glu-Val-Gly-Lys-Ala-Met-Tyr-Ala-Pro-Pro-Ile-Ser-Gly-Gln-Ile-Arg-Cys-X Peptide 126 (SEQ NO. 1)

(ii) Gln-Ser-Val-Glu-Ile-Asn-Cys-Thr-Arg-Pro-Asn-Asn-Asn-Thr-Arg-Lys-Ser-Ile-Arg-Ile-Gln-Arg-Gly-Pro-Gly-Arg-Ala-Phe-Val-Thr-Ile-Gly-Lys-X Peptide 127 (SEQ NO. 11)

(iii) analogues thereof, and (iv) mixtures thereof, wherein X is —OH or —$NH_2$.

It is contemplated that the peptides and their analogues will include about 15 amino acids, usually fewer than 50, more usually fewer than about 40 amino acids and correspond to one of the following sequences:

Cys-Arg-Ile-Lys-Gln-Ile-Ile-Asn-Met-Trp-Gln-Glu-Val-Gly-Lys-Ala- Met-Tyr-Ala-Pro-Pro-Ile-Ser-Gly-Gln-Ile-Arg-Cys-X Peptide 126

Gln-Ser-Val-Glu-Ile-Asn-Cys-Thr-Arg-Pro-Asn-Asn-Asn-Thr-Arg-Lys-Ser-Ile-Arg-Ile-Gln-Arg-Gly-Pro-Gly-Arg-Ala-Phe-Val-Thr-Ile-Gly-Lys-X Peptide 127 (SEQ NO. 11)

wherein X is —OH or —$NH_2$.

The peptide segments should be as small as possible, while still maintaining substantially all of the immunoreactivity of the larger peptide. In some instances it may be desirable to join two or more peptides which are non-overlapping into a longer peptide. The peptides may also be used as individual peptides, which separately or together provide equivalent sensitivity or efficacy to the parent.

To accommodate strain to strain variations among different isolates, adjustments for conservative substitutions and selection among the alternatives, where non-conservative substitutions are involved, or deletions or additions of amino acids may be made as analogue peptides.

Such conservative or non-conservative substitutions, deletions or additions of amino acids may be made, as shown for example in Table IIa and IIb, to more effectively mimic the differing epitopes of the different retroviral strains as long as the specific immunoreactivity of the peptide to HIV antibodies is preserved.

These peptides can be used individually or in mixtures for the detection of antibodies to HIV gp120 envelope protein in a physiological sample. Depending on the nature of the assay protocol, the peptides may be labelled or unlabelled, bound to a solid surface, polymeric or conjugated to a carrier or the like.

A specific peptide embodying the present invention is Peptide 126, a 28mer, has the following amino acid sequence:

Cys-Arg-Ile-Lys-Gln-Ile-Ile-Asn-Met-Trp-Gln-Glu-Val-Gly-Lys-Ala-Met-Tyr-Ala-Pro-Pro-Ile-Ser-Gly-Gln-Ile-Arg-Cys-X Peptide 126 (SEQ NO. 1)

where X is —OH or —$NH_2$ or its analogue.

Another specific peptide embodying the present invention is Peptide 127, a 33mer, having the following amino acid sequence:

Gln-Ser-Val-Glu-Ile-Asn-Cys-Thr-Arg-Pro-Asn-Asn-Asn-Thr-Arg-Lys-Ser-Ile-Arg-Ile-Gln-Arg-Gly-Pro-Gly-Arg-Ala-Phe-Val-Thr-Ile-Gly-Lys-X Peptide 127 (SEQ NO. 11)

wherein X is —OH or —$NH_2$ or an analogue of the peptide.

TABLE IIa

PEPTIDE 126 AND ITS ANALOGUES

| Isolates | Amino Acid Sequences |
|---|---|
| *BH10 | CysArgIleLysGlnIleIleAsnMetTrpGlnGluValGlyLysAlaMetTyrAlaPro |
| (SEQ NO. 1) | ProIleSerGlyGlnIleArgCys |
| BRU | CysArgIleLysGlnPheIleAsnMetTrpGlnGluValGlyLysAlaMetTyrAlaPro |
| (SEQ NO. 2) | ProIleSerGlyGlnIleArgCys |
| PV22 | CysArgIleLysGlnPheIleAsnMetTrpGlnGluValGlyLysAlaMetTyrAlaPro |
| (SEQ NO. 2) | ProIleSerGlyGlnIleArgCys |
| HXB2 | CysArgIleLysGlnIleIleAsnMetTrpGlnLysValGlyLysAlaMetTyrAlaPro |
| (SEQ NO. 3) | ProIleSerGlyGlnIleArgCys |
| SF2 | CysArgIleLysGlnIleIleAsnMetTrpGlnGluValGlyLysAlaMetTyrAlaPro |
| (SEQ NO. 4) | ProIleGlyGlyGlnIleSerCys |
| WMJ2 | CysArgIleLysGlnIleIleAsnMetTrpGlnGlyValGlyLysAlaMetTyrAlaPro |
| (SEQ NO. 5) | ProIleGlnGlyGlnIleArgCys |
| NY5 | CysArgIleLysGlnIleIleAsnMetTrpGlnGluValGlyLysAlaIleTyrAlaPro |
| (SEQ NO. 6) | ProIleSerGlyGlnIleArgCys |
| RF | CysArgIleLysGlnIleValAsnMetTrpGlnGluValGlyLysAlaMetTyrAlaPro |
| (SEQ NO. 7) | ProIleSerGlyGlnIleLysCys |
| MAL | CysArgIleLysGlnIleIleAsnMetTrpGlnLysThrGlyLysAlaMetTyrAlaPro |
| (SEQ NO. 8) | ProIleAlaGlyValIleAsnCys |
| HIV-2 | CysHisIleLysGlnIleIleAsnThrTrpHisLysValGlyArgAsnValTyrLeuPro |
| (SEQ NO. 9) | ProArgGluGlyGluLeuSerCys |
| SIV | CysHisIleHisGlnIleIleAsnThrTrpHisLysValGlyLysAsnValTyrLeuPro |
| (SEQ NO. 10) | ProArgGluGlyAspLeuThrCys |

Peptide 126 is derived from a region of the gp120 envelope protein of a prototype HIV (BH10) encoded from bp7053 to bp7136. This sequence represents a more conserved region of the gp120. Analogues with amino acid sequences derived from this region representing various HIV isolates may be constructed in accordance with this table.

TABLE IIb

PEPTIDE 127 AND ITS ANALOGUES

| Isolates | Amino Acid Sequences |
|---|---|
| BH10 (SEQ. NO. 11) | GlnSerValGluIleAsnCysThrArgProAsnAsnAsnThrArgLysSerIleArgIle |
| BRU (SEQ NO. 11) | ------------------------------ |
| PV22 (SEQ NO. 11) | ------------------------------ |
| HXB2 (SEQ NO. 12) | TheSerValGluIleAsnCysThrArgProAsnAsnAsnThrArgLysArgIleArgIle GlnArgGlyProGlyArgAlaPheValThrIleGlyLys |
| SF2 (SEQ NO. 13) | GluSerValAlaIleAsnCysThrArgProAsnAsnAsnThrArgLysSerIleArgTyr GlnArgGlyProGlyArgAlaPheHisThrThrGlyArg |
| SC (SEQ NO. 14) | GluAlaValGluIleAsnCysThrArgProAsnAsnAsnThrThrArgSerIleHisIle GlnProGlyArgAlaPheTyrAlaThrLysAsp |
| WMJ2 (SEQ NO. 15) | GluSerValGluIleAsnCysThrArgProTyrAsnAsnValArgArgSerLeuSerIle GlyProGlyArgAlaPheArgThrArgGluIle |
| MN (SEQ NO. 16) | GluSerValGlnIleAsnCysThrArgProAsnTyrAsnLysArgLysArgIleHisIle GlyProGlyArgAlaPheTyrThrThrLysAsn |
| NY5 (SEQ NO. 17) | LysSerValGluIleAsnCysThrArgProAsnAsnAsnThrLysLysGlyIleAlaIle GlyProGlyArgThrLeuTyrAlaArgGluLys |
| RF (SEQ NO. 18) | AlaSerValGlnIleAsnCysThrArgProAsnAsnAsnThrArgLysSerIleThrLys GlyProGlyArgValIleTyrAlaThrGlyGln |
| MAL (SEQ NO. 19) | GluThrValThrIleAsnCysThrArgProGlyAsnAsnThrArgArgGlyIleHisPhe GlyProGlyGlnAlaLeuTyrThrThrGlyIle |
| HIV-2 (SEQ NO. 20) | TyrAsnLeuSerCysHisCysLysArgProGlyAsnLysIleValLysGlnIleMetLeu MetSerGlyGlyHisArgValPheHisSerHisTyrGln |
| SIV | TyrAsnLeuThrMetLysCysArgArgProGlyAsnLysThrValLeuProValThrIle MetSerLeuValPheHisSerGlnProVal (compared to HIV-2) |

*Blank spaces reserved for maximal sequence alignment
Peptide 127 is derived from a region of the gp120 envelope protein of a prototype HIV strain (BH10) encoded from bp6669 to bp6767. This sequence represents a variable region of gp120. Analogues of this sequence from various strains of HIV may be constructed in accordance with this table.

The peptides can be prepared in several ways. The peptides, because of their relatively small size, are easily synthesized by the solid phase strategy as developed by Merrifield (18) which is herein incorporated by reference. Various commercially available automatic peptide synthesizers with known protocols can be used for peptide synthesis and production.

Peptides of this invention can also be prepared via recombinant DNA technology. In their preparation, a nucleotide sequence coding for the desired peptide or peptides in a tandem arrangement, representing the selected epitopes and their analogues, can be prepared using a conventional method for DNA synthesis. The synthesized oligonucleotides are ligated for the construction of a synthetic gene encoding such artificial protein containing the specified epitopes designated by the amino acid sequences of Peptides 126 and 127 or their analogues. The synthetic gene so constructed can then be transfected for optimal expression in various host cells.

The peptide or analogues may also be conjugated or polymerized. Conjugates of the peptides or their analogues with protein carriers such as serum albumins, heparin, etc. which are known to be useful to provoke B cell responses can be made. The conjugates may be prepared by incubating the protein carrier with the peptide in the presence of glutaraldehyde.

Polymers of the peptides or their analogues can also be synthesized. For example, dimeric, tetrameric, octameric, and decahexyl forms of the peptides or their analogues can be synthesized onto a branching poly-L-lysine as described in Example 6. The branching poly-L-lysine can be $Lys_8Lys_4Lys_2Lys_2Lys$, $Lys_4Lys_2Lys$, $Lys_2Lys$, Lys; the last Lys can be attached to Y as in $Lys_4Lys_2Lys$-Y, wherein Y is —OH, —$NH_2$ or an amino acid containing no side chain functional group, such as alanine, valine, glycine, etc. Y can be inserted to facilitate synthesis onto the 4-methylbenzhydrylamine resin. The conjugate and polymers of the peptides or their analogues are also useful in the present invention.

The peptides of the present invention show a high degree of immunoreactivity with antibodies to HIV. A comparison of the results obtained for known serum samples by EIA using Peptide 126 or Peptide 127 as the solid phase immunoadsorbent with results previously obtained for these known serum samples show that both peptides are highly specific in their immunoreactivity to antibodies to HIV. This shows that both Peptide 126 and Peptide 127 define highly reactive epitopes.

Analysis of seropositivity with Peptide 126 and Peptide 127 by EIA on 30 well characterized sera with known neutralizing antibody titers revealed a high degree of correlation as calculated by Spearman Rank Correlation Coefficient, $r=0.949$, $p<0.001$ for Peptide 126 and $r=0.888$, $p<0.001$ for Peptide 127. This means that a rapid EIA method using Peptide 126 or Peptide 127 as the immunoadsorbent can be employed to replace the time consuming method for the measurement of serum neutralizing antibody titers.

HIV neutralizing antibody titers have previously been determined by reverse transcriptase assay. For example, Prince et al. described a semi-automated microtiter assay which requires the culturing of serum specimens with HIV for 14 to 21 days followed by repeat measurement of reverse transcriptase activity in twelve replicates to obtain significant data. However, little or no correlation was found between the neutralizing antibody titers as determined by the reverse transcriptase assay, and the immunoreactivity determined by an EIA method using deactivated virus as the immunosorbent (20).

In contrast, a high degree of correlation was found between the neutralizing antibody titers determined by reverse transcriptase assay and the peptide 126 and peptide 127 based EIAS. Thus, an EIA using the peptides of the present invention can be employed to select high neutralizing antibody containing plasma specimens for the production of human gamma globulin fraction for use in passive immunization and to measure the level of HIV neutralizing antibody titers in various serum and plasma specimens.

The peptides of the present invention are also useful as immunogens to elicit the production of high titer HIV antibodies in mammals with protective value. This shows that the peptides are ultimately useful as vaccines for the prevention of HIV infection.

The invention is illustrated in the following examples wherein these peptides, analogues or segments thereof in a free, conjugated, or polymeric form are used as either an immunosorbent or as an immunogen. These examples are offered to illustrate the invention and are not to be used to limit the scope of the present invention.

EXAMPLE 1

Detection of Antibodies to HIV gp120 by Peptide Based EIA

Wells of 96 well plates were coated at 4° C. over night with Peptide 126 or Peptide 127, both prepared by standard solid phase peptide synthesis employing t-Boc chemistry on a BIOSEARCH 9500 automated synthesizer and cleaved from the resin by HF treatment. Each of the peptides was coated onto the wells at lug per well in 100 uL 10 mM $NaHCO_3$ buffer, pH 9.5. The wells were washed three times with phosphate-buffered saline (PBS) and then incubated with 250 uL of 3% by weight gelatin in PBS at 37° C. for 1 hour to block nonspecific protein binding sites, followed by three more washes with PBS containing 0.05% by volume Tween 20. Test sera from well-characterized patients or volunteered donors were diluted 1:20 volume to volume with PBS containing 20% by volume normal goat serum, 1% by weight gelatin, and 0.05% by volume Tween 20. 200 uL of the diluted sera were added to each well and allowed to react for 15 min at 37° C. The wells were then washed three times with 0.05% by volume Tween 20 in PBS in order to remove unbound antibodies. 100 uL Horseradish peroxidase conjugated goat anti-human IgG at a 1:3000 dilution in 1% by volume normal goat serum, 0.05% by volume Tween 20 in PBS was added to each well at 37° C. for 15 min as a second antibody tracer to bind with the antibody-antigen complex formed in positive wells.

The wells were washed five times with 0.05% by volume Tween 20 in PBS to remove unbound antibody and reacted with 100 uL of the substrate mixture containing 0.04% by weight o-phenylenediamine (OPD) and 0.012% by volume hydrogen peroxide in sodium citrate buffer, pH 5.0. This substrate mixture was used to detect the peroxidase label by forming a color product. Reactions were stopped by the addition of 50 uL of 1M $H_2SO_4$, and the color yield measured using an EIA reader at 492 nm. Absorbance readings greater than three times the average readings of 100 normal blood donor sera were taken as positive. The results are shown in Table III.

TABLE III

DETECTION OF ANTIBODIES TO HIV BY EIA USING PEPTIDE 126 OR PEPTIDE 127 AS SOLID PHASE IMMUNOADSORBENT

| SUBJECT | NO. POSITIVE WITH gp41/p24 HIV-EIA SCREENING ASSAY*/ NO. TESTED | NO. POSITIVE WITH GP120 PEPTIDE 126/ NO. TESTED | NO. POSITIVE WITH GP120 PEPTIDE 127/ NO. TESTED |
|---|---|---|---|
| 1. AIDS | 15/15 | 13/15 | 10/15 |
| 2. ARC | 8/8 | 4/8 | 6/8 |
| 3. HIV SEROPOS. INDIVIDUALS | 17/17 | 16/17 | 12/17 |
| 4. LYMPHOID-LEUKEMIA MALIGNANCIES | 0/37 | 0/37 | 0/37 |
| 5. HTLV-I SEROPOS. INDIVIDUALS (ATL) | 0/50 | 0/50 | 0/50 |
| 6. AUTOIMNUNE DISEASES | 0/19 | 0/19 | 0/19 |
| 7. NORMAL BLOOD DONORS | 0/115 | 0/135 | 0/135 |

*Most of the positive specimens gave an $A_{492nm}$ of over 2.00.

Figure 1B:
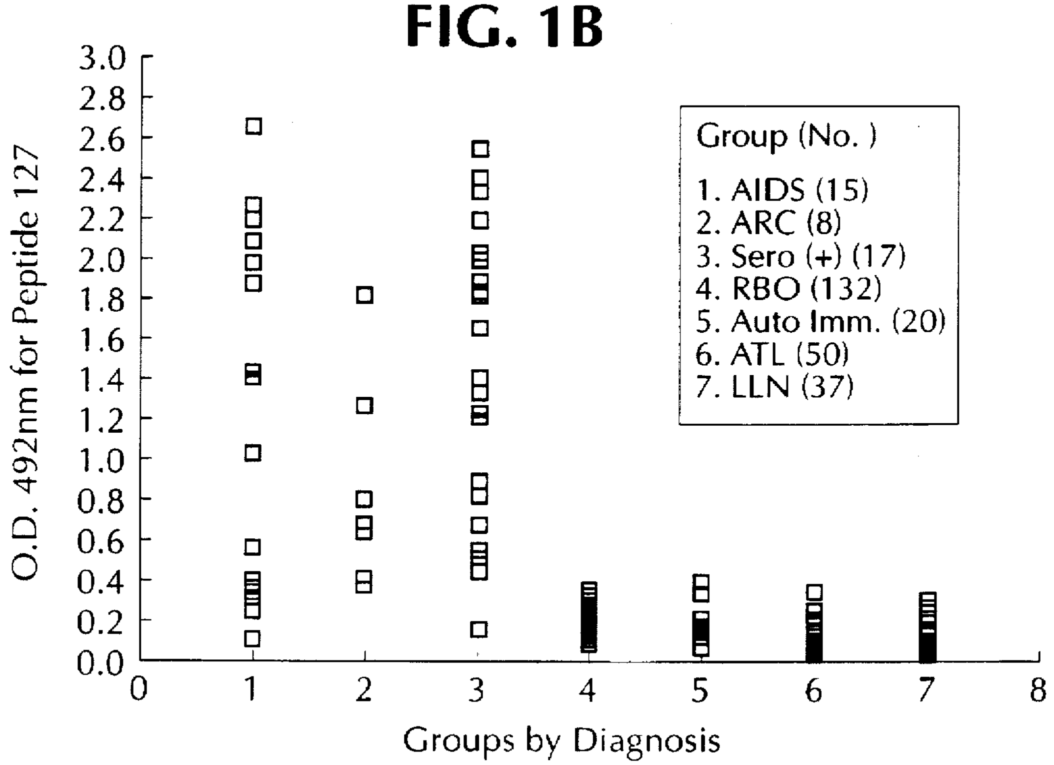

Histograms depicting the $A_{492nm}$ values of each clinical specimen are presented in FIGS. 1*a* and 1*b*. Both peptide based EIAs (Peptide 126 and Peptide 127) demonstrated a reasonable degree of specificity.

Peptide 126 based EIA gave higher absorbance readings for those HIV positive specimens and detected a larger HIV seropositive population (82.5%) than Peptide 127 based EIA (70%).

EXAMPLE 2

Detection of HIV-gp120 seropositivity by employing either Peptide 126 or Peptide 127 as the immunoadsorbent is unique to the two peptides described in this invention. A serum titration experiment was conducted using Peptide 126, Peptide 127, a third gp120 peptide with an amino acid sequence of Arg-Pro-Gly-Gly-Gly-Asp-Met-Arg-Asp-Asn-Trp-Arg-Ser-Glu-Leu-Tyr-Lys-Tyr-Lys-Val-Val-Lys-Ile-Glu-Pro-Leu-Gly-Val-Ala-Pro (Peptide 065) (SEQ NO.37) and a fourth gp12O peptide which is an 8mer with an amino acid sequence of Ala-Ser-Thr-Thr-Thr-Asn-Tyr-Thr (Peptide T). Neither "Peptide 065" nor "Peptide T" showed any immunoreactivity with sera from HIV seropositive individuals. See Table IV.

TABLE IV

| SPECIFIC HIV gp120 IMMUNOREACTIVITY ASSOCIATED WITH PEPTIDES 126 and 127 | | | | |
|---|---|---|---|---|
| Dilution Serum No. | $A_{492nm}$-EIA | | | |
| N-9-13 | Peptide 126 | Peptide 127 | Peptide 065 | Peptide T |
| 1:20 | 2.64 +/- 0.02 | 2.52 +/- 0.01 | 0.04 +/- 0.01 | 0.02 +/- 0.00 |
| 1:40 | 2.47 +/- 0.01 | 2.04 +/- 0.01 | 0.01 +/- 0.01 | 0.03 +/- 0.00 |
| 1:80 | 2.14 +/- 0.02 | 1.41 +/- 0.01 | 0.06 +/- 0.02 | 0.02 +/- 0.00 |
| 1:160 | 1.63 +/- 0.02 | 0.93 +/- 0.01 | 0.05 +/- 0.02 | 0.00 +/- 0.00 |
| 1:320 | 1.04 +/- 0.01 | 0.55 +/- 0.00 | 0.03 +/- 0.00 | 0.02 +/- 0.00 |
| 1:640 | 0.62 +/- 0.00 | 0.32 +/- 0.00 | 0.04 +/- 0.01 | 0.03 +/- 0.00 |
| 1:1280 | 0.36 +/- 0.00 | 0.19 +/- 0.00 | 0.04 +/- 0.00 | 0.03 +/- 0.00 |

Figure 2A:
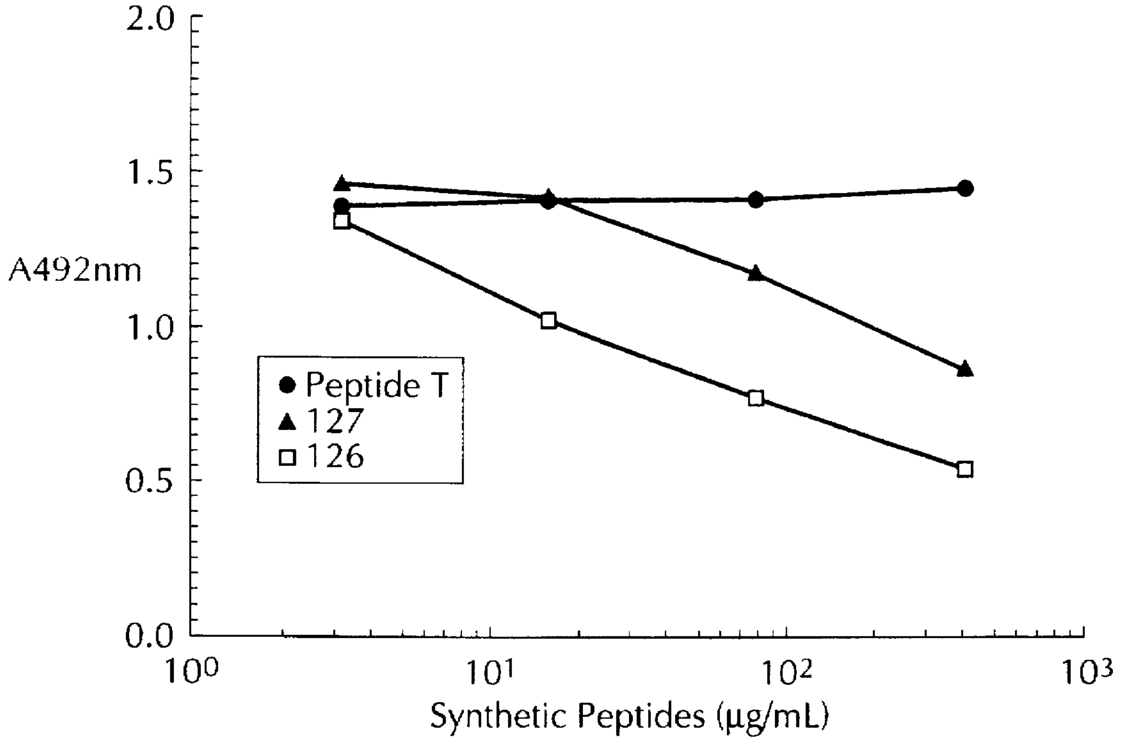
FIGS. 2*a* and 2*b* show the specificity of the immunoreactivities of Peptide 126 and Peptide 127 with HIV serum antibodies. An increased amount of Peptide 126, Peptide 127 or Peptide T is pre-incubated with serum antibodies from a representative HIV positive sample (N-9-13) followed by EIA using either Peptide 126 (FIG. 2*a*) or Peptide 127 (FIG. 2*b*) as the solid phase immunoadsorbent.
Figure 2B:
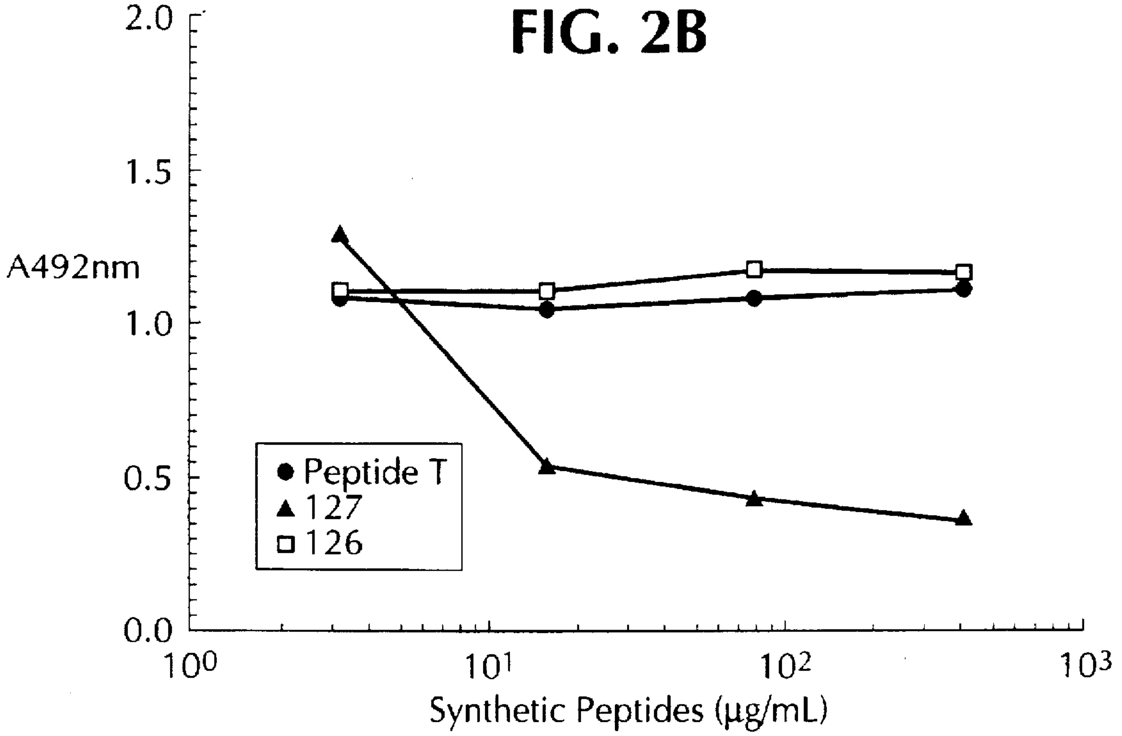

Serial serum titrations showed that the immunoreactivity of Peptide 126 and Peptide 127 with HIV seropositive specimens are specific where no cross reactions between the two peptides were found as shown in FIGS. 2*a* and 2*b*. Only Peptide 127, but not Peptide 126 nor Peptide T, inhibited the antibody reactivity to Peptide 127. Similarly, Peptide 126 but not Peptide T and to a much less extent Peptide 127, inhibited the antibody reactivity to Peptide 126.

EXAMPLE 3

Figure 3:
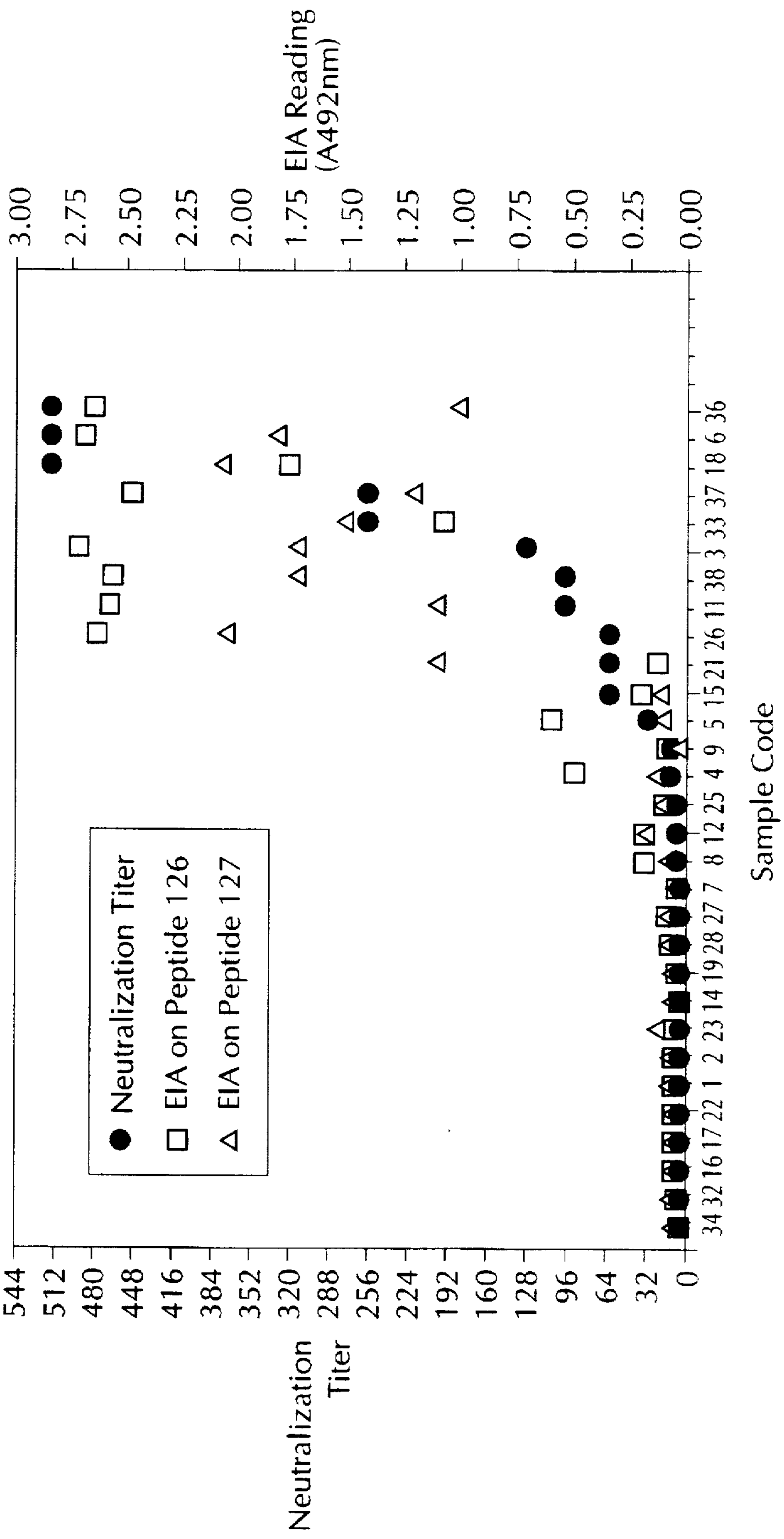
FIG. 3 shows the correlation of the $A_{492nm}$ results obtained by EIA, using Peptide 126 and Peptide 127 as the immunoadsorbents, and the neutralizing antibody titer of 30 serum samples.

A total of 30 sera, which have been titered for their ability to neutralize HIV infection in cell culture using a method described by Prince (20), were tested at a 1:45 dilution by an EIA procedure employing (i) a mixture of three HIV peptides known to be highly specific to antibodies to HIV: an 11mer peptide from the p24 region, a 19mer peptide and a 21mer peptide from the gp41 region (UBI, Lake Success, N.Y.), (ii) Peptide 126, and (iii) Peptide 127 as the solid phase immunoadsorbent antigens respectively. Results of this study are presented in Table V. Further analysis of the data indicated a high degree of correlation between the neutralizing antibody titer of each serum and its immunoreactivity as demonstrated by the respective $A_{492nm}$ readings with either Peptide 126 or Peptide 127 (FIG. 3). The calculated Spearman Rank correlation coefficients between neutralizing antibody titer and the respective EIA absorbance readings are r=0.949, p<0.001 for Peptide 126; and r=0.888, p<0.001 for Peptide 127.

Present methods employed to measure serum neutralizing antibody titers take about 14 to 21 days to perform and are subject to many experimental errors. This high degree of correlation between results obtained by the peptide based EIA method employing Peptide 126 or Peptide 127 as the solid phase immunoadsorbent and the neutralizing antibody titers determined by reverse transcriptase activity indicates that these peptide based EIAs are useful for predicting the presence of neutralizing antibodies in serum or plasma.

TABLE V $A_{492nm}$ OF SERA BY EIAs EMPLOYING A COMBINATION OF gp41/p24 PEPTIDES, PEPTIDE 126 OR PEPTIDE 127 AS IMMUNOADSORBENT ANTIGENS

| | | $A_{492nm}$-EIA | | |
|---|---|---|---|---|
| Sample Code | Neutralization titer | Peptide 126 (gp 120) | Peptide 127 (gp 120) | HIV screening EIA (gp41/ p24 peptides) |
| 1 | <1:4 | 0.05 | 0.09 | 0.07 |
| 2 | <1:4 | 0.05 | 0.09 | 0.06 |
| 3 | 1:128 | 2.69 | 1.71 | 2.88 |
| 4 | 1:16 | 0.50 | 0.14 | 1.13 |
| 5 | 1:32 | 0.68 | 0.12 | 1.68 |
| 6 | ≧1:512 | 2.67 | 1.89 | 2.92 |
| 7 | 1:6 | 0.04 | 0.05 | 0.07 |
| 8 | 1:8 | 0.20 | 0.07 | 2.12 |
| 11 | 1:100 | 2.56 | 1.10 | 2.62 |
| 12 | 1:8 | 0.20 | 0.22 | 0.13 |
| 14 | 1:4 | 0.06 | 0.08 | 0.07 |
| 15 | 1:64 | 0.21 | 0.13 | 1.00 |
| 16 | 1:4 | 0.05 | 0.07 | 0.09 |
| 17 | 1:4 | 0.05 | 0.07 | 0.06 |
| 18 | 1:512 | 1.75 | 2.05 | 1.50 |
| 19 | <1:4 | 0.06 | 0.07 | 0.10 |
| 21 | 1:64 | 0.14 | 1.19 | 1.71 |
| 22 | <1:4 | 0.05 | 0.07 | 0.07 |
| 23 | <1:4 | 0.05 | 0.13 | 0.06 |
| 25 | 1:8 | 0.09 | 0.11 | 0.13 |
| 26 | 1:64 | 2:61 | 2.06 | 2.52 |
| 27 | 1:4 | 0.09 | 0.07 | 0.27 |
| 28 | 1:4 | 0.07 | 0.08 | 0.12 |
| 29 | 1:64 | 0.08 | 0.08 | 0.19 |
| 32 | <1:4 | 0.04 | 0.08 | 0.07 |
| 33 | 1:256 | 1.07 | 1.53 | 0.54 |
| 34 | <1:4 | 0.03 | 0.08 | 0.07 |
| 36 | ≧1:512 | 2.62 | 0.98 | 2.69 |
| 37 | 1:256 | 2.45 | 1.16 | 2.17 |
| 38 | 1:100 | 2.54 | 1.73 | 2.59 |

EXAMPLE 4

Figure 4A:
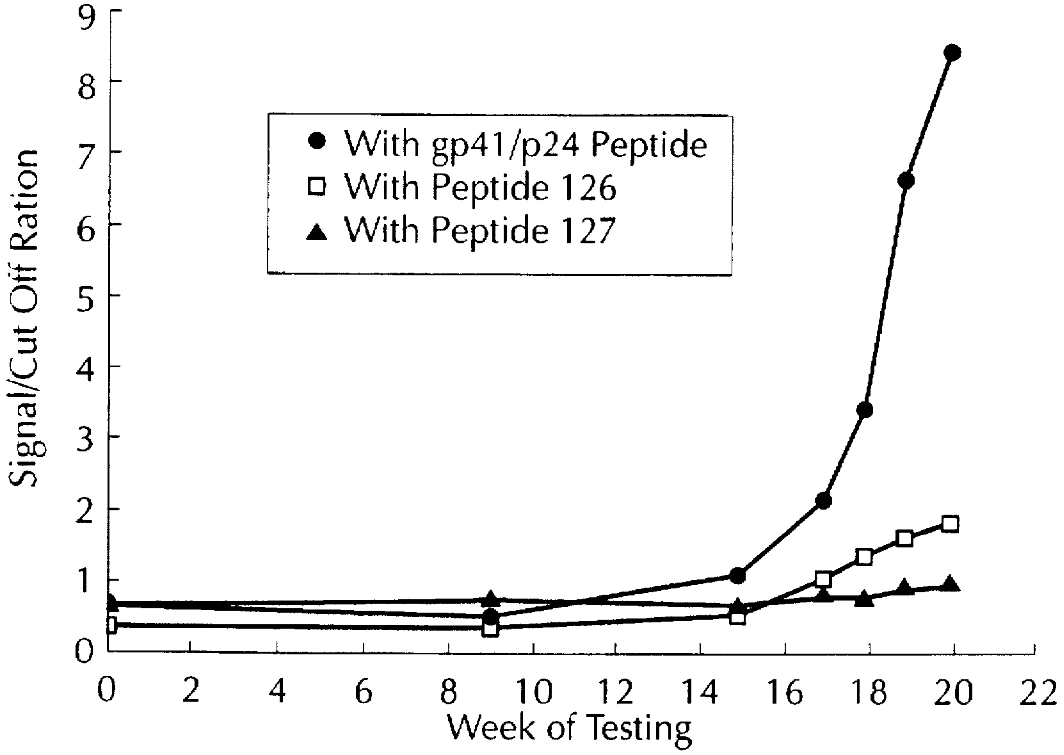
FIGS. 4*a* and 4*b* shows the respective immunoreactivity of Peptide 126 and Peptide 127 in comparison with an EIA using a mixture of gp41/p24 peptides (United Biomedical, Lake Success, N.Y.) which has been shown to be specific for detecting antibodies to HIV with a series of serum specimens derived from Patients A and B who underwent seroconversion to become HIV antibody positive. When the signal/cutoff ratio derived from the EIA using the gp41/p24 peptide mixture exceeds 1, HIV infection in each of the patients is detected.
Figure 4B:
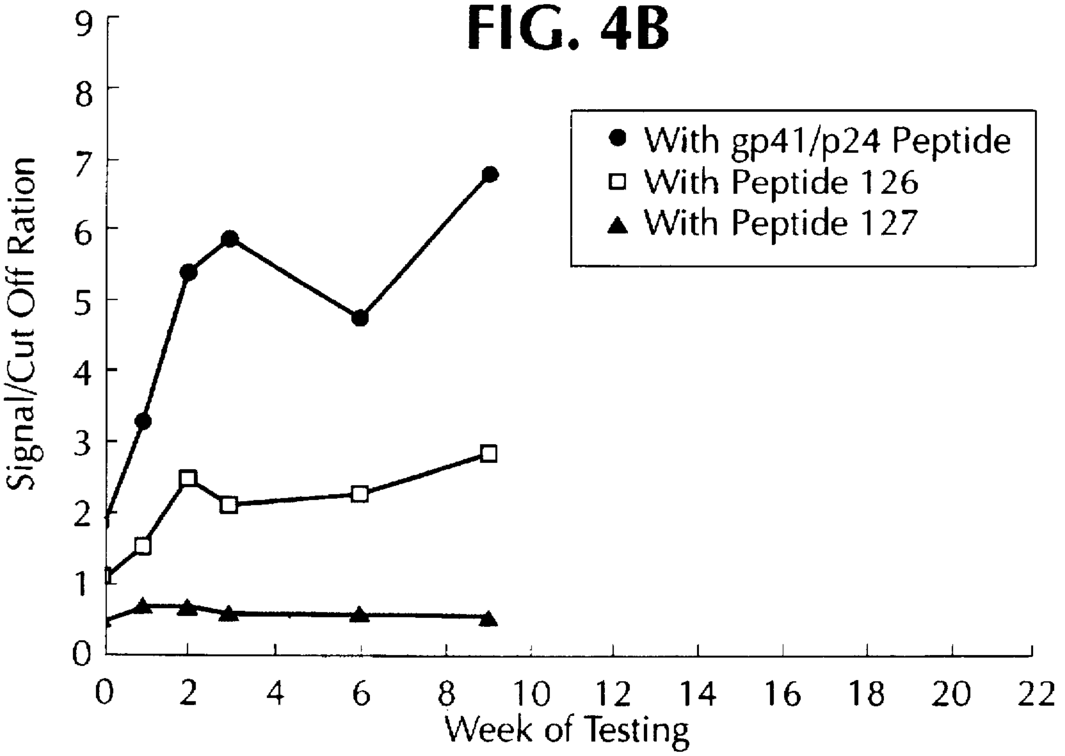
Figure 5A:
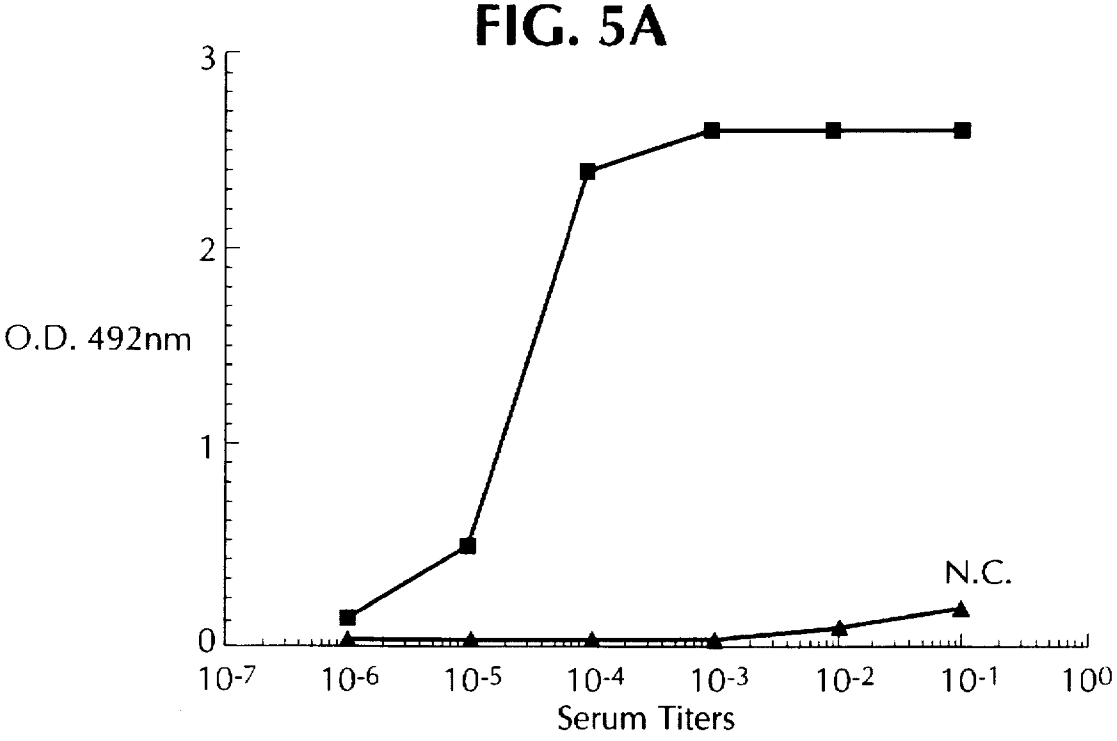
FIGS. 5*a*, 5*b*, 5*c* and 5*d* show the guinea pig serum antibody titers after initial immunization and one boost with (i) Peptide 126-BSA (FIG. 5*a*), (ii) Peptide 127-BSA (FIG. 5*c*), (iii) Peptide 126 octamer (FIG. 5*b*), and (iv) Peptide 127 octamer (FIG. 5*d*). (N.C.
Figure 5B:
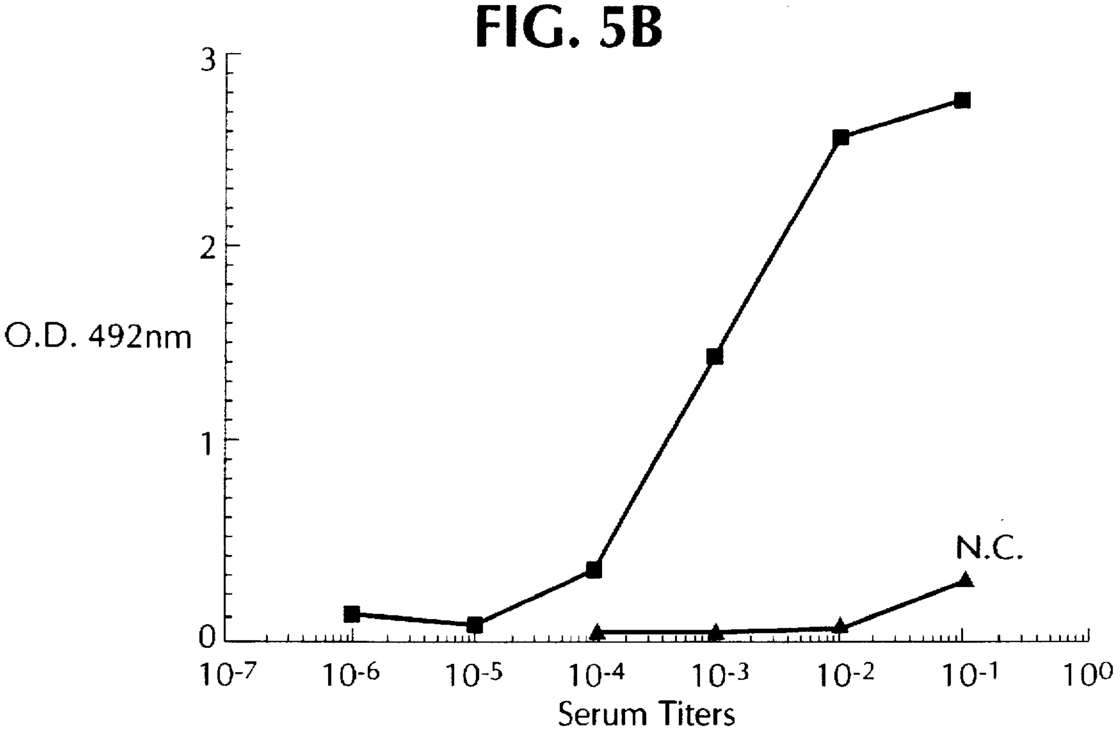
Figure 5C:
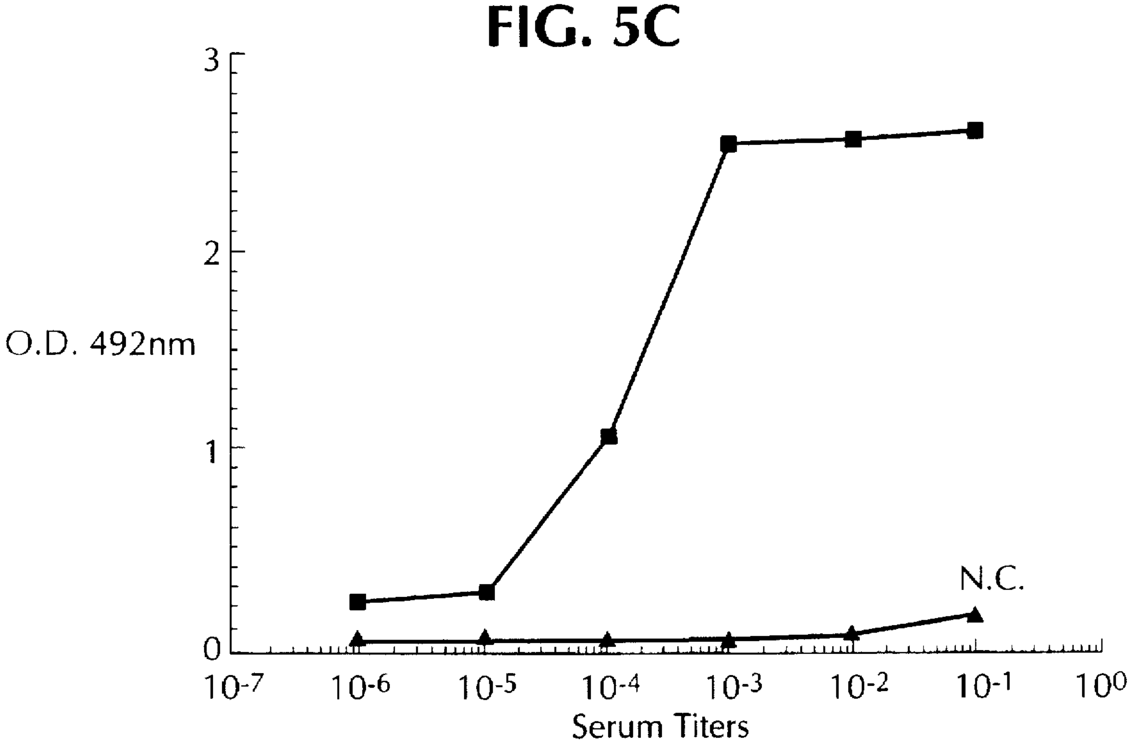
Figure 5D:
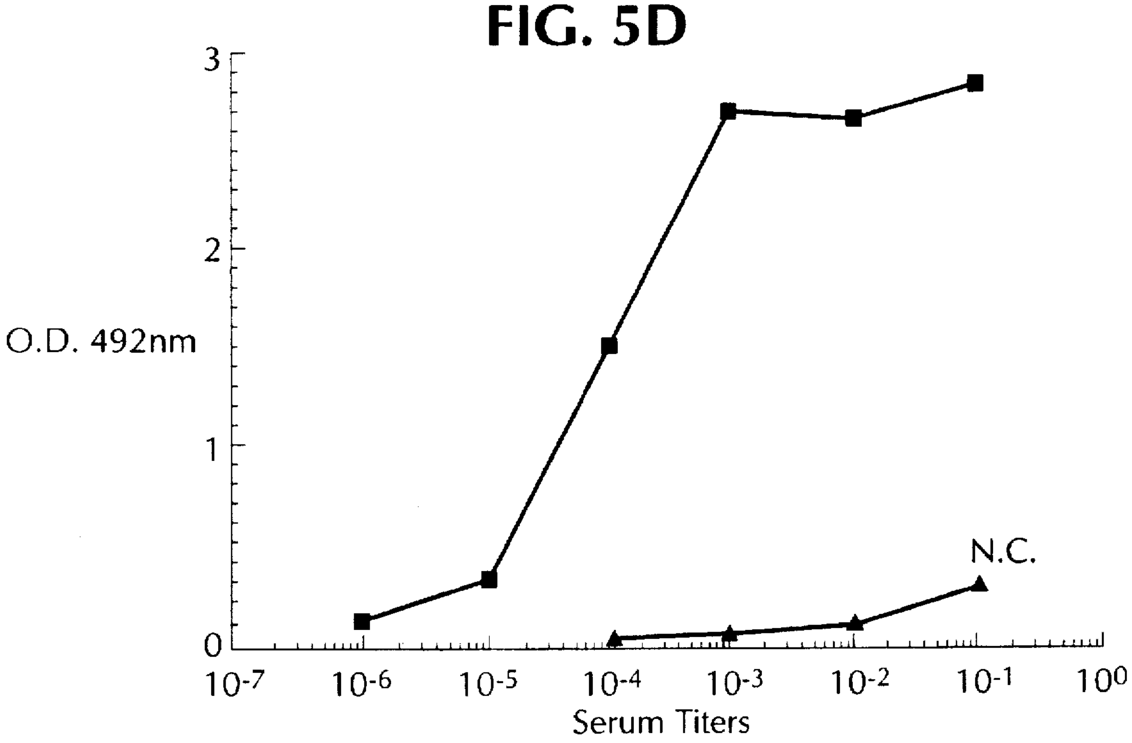
Figure 6A:
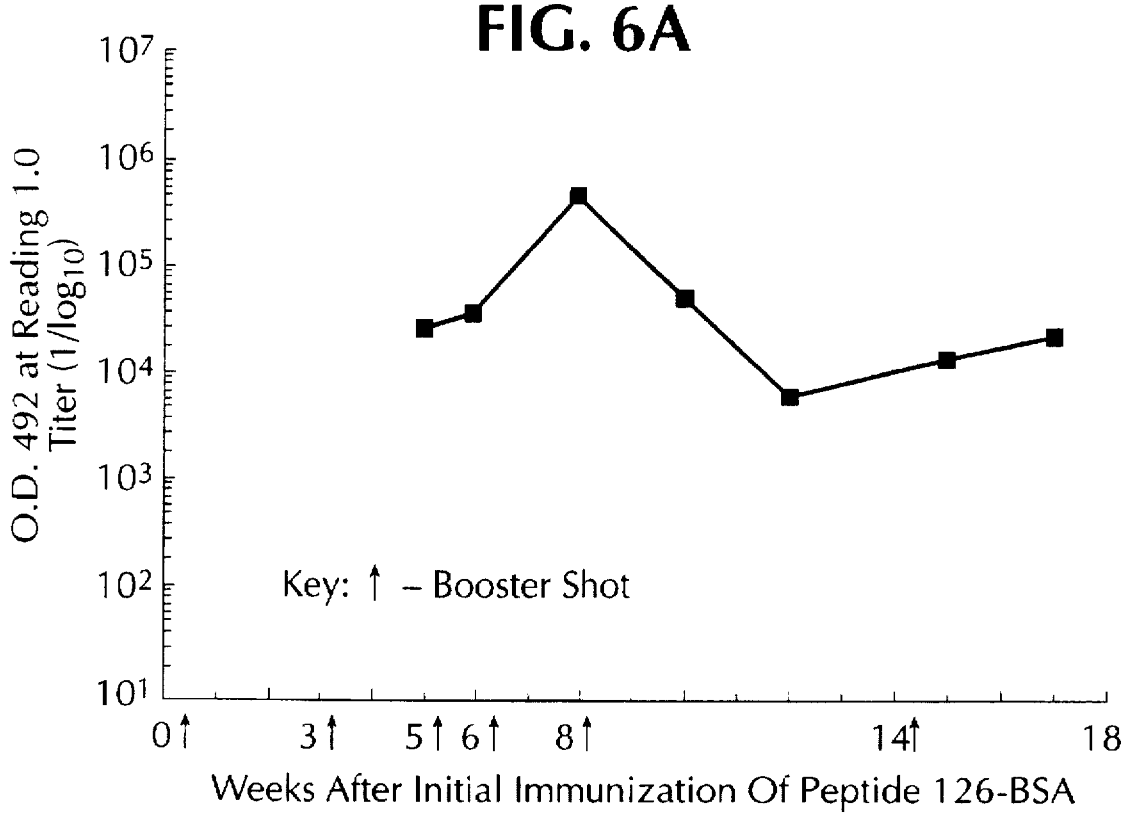
FIGS. 6*a*, 6*b*, 6*c* and 6*d* show that sustained high titers of serum antibodies were produced by immunization with (i) Peptide 126-BSA (FIG. 6*a*), (ii) Peptide 127-BSA (FIG. 6*c*), (iii) Peptide 126 octamer (FIG. 6*b*), and (iv) Peptide 127 octamer (FIG. 6*d*).
Figure 6B:
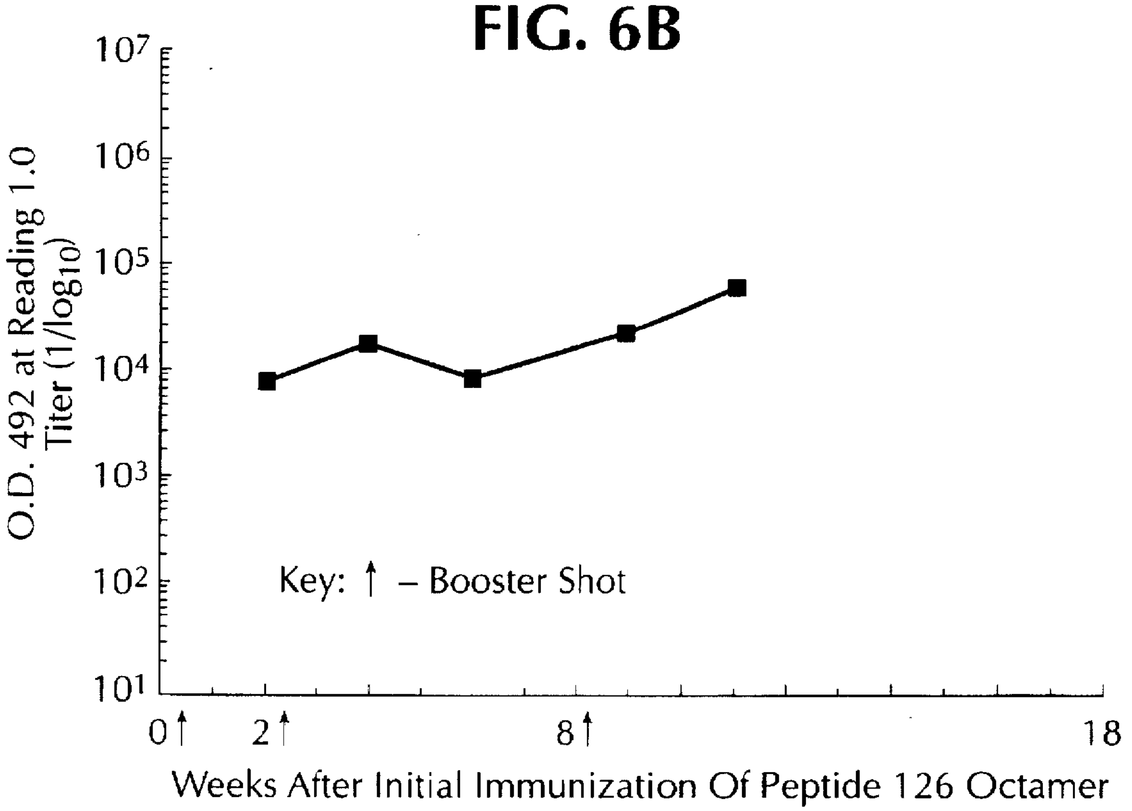
Figure 6C:
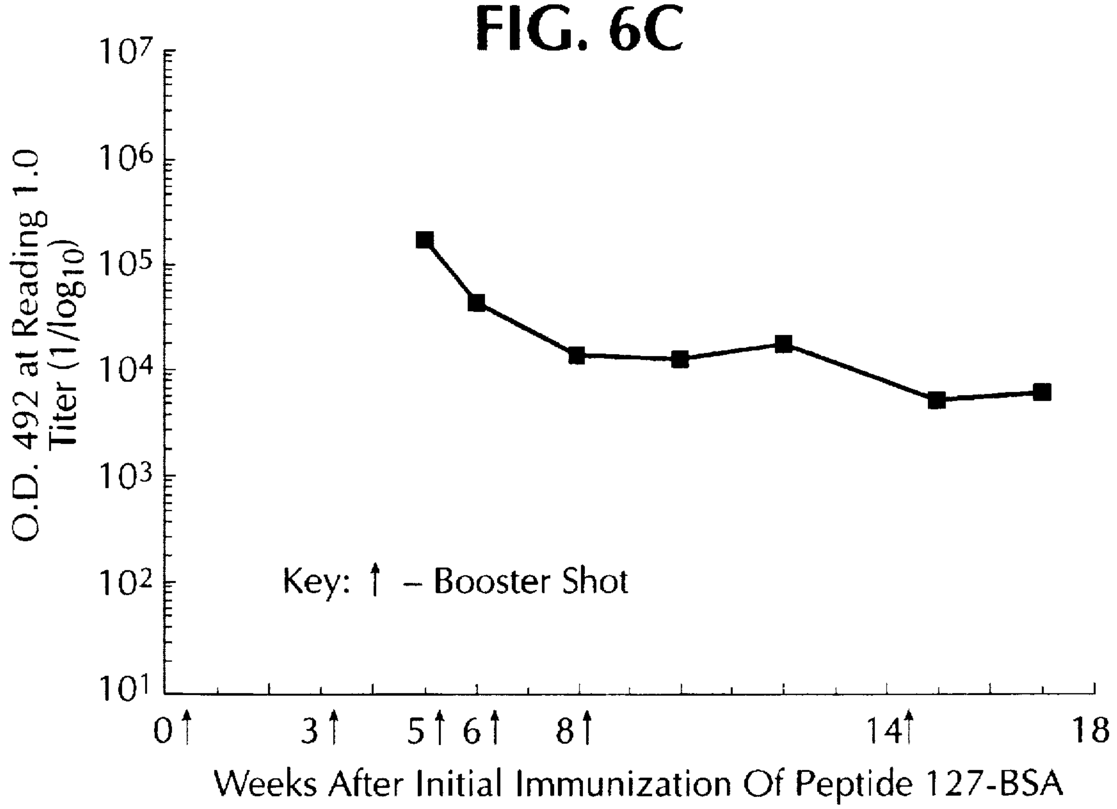
Figure 6D:
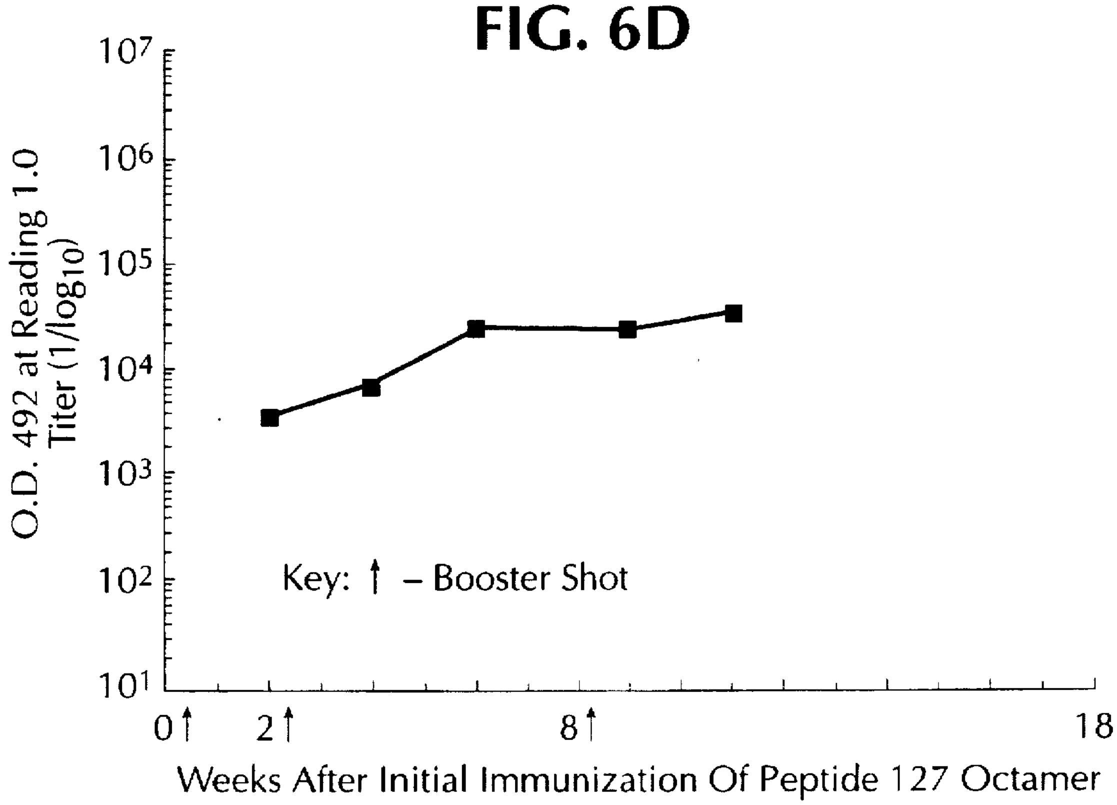

A total of 13 sequential bleedings from two HIV infected patients collected during the period of seroconversion were tested for reactivity to HIV using a mixture of three peptides derived from the gp41/p24 region (HIV-EIA test kit, UBI, Lake Success, N.Y.), Peptide 126, or Peptide 127 as the immunoadsorbent in an EIA method. The results show that the latency period for the development of antibodies to gp120 Peptide 126 is longer than that for the gp41/p24 peptides; whereas the latency period for the development of antibodies to gp120 Peptide 127 was even longer than that of peptide 126, occurring at a very late stage during the course of infection. See FIGS. 4*a* and 4*b*.

EXAMPLE 5

Conjugation of Peptide 126 and Peptide 127 with Bovine Serum Albumin (BSA)

5 mg of BSA was dissolved in 5mL of PBS with gentle sonication. To the supernatant was added 4 mg of HF cleaved Peptide 126 or Peptide 127 followed by the addition of 40 uL glutaldehyde (25%) to result in a final glutaldehyde concentration of 0.2%. The peptide-BSA and glutaldehyde mixture was incubated overnight at 4° C. followed by an extensive dialysis with multiple changes (200× of its volume) of PBS. The dialyzed peptide-BSA conjugate was then used together with either complete or incomplete Freund's adjuvant for injection into each animal according to an immunization program.

EXAMPLE 6

Synthesis of Lysine Polymers of Peptides 126 and 127

The synthesis of an octameric form of Peptide 126 and Peptide 127 was initiated on a 4-methylbenzhydrylamine (MBHA) resin onto which three successive cycles of Boc-Lys (BOZ), i.e., di-t-Boc Lys, coupling were conducted to generate a branching Lys peptide core with eight reactive amino ends. The synthesis of Peptide 126 or Peptide 127 on this octameric lysine resin with eight reactive amino ends thereafter was similar to the synthesis of a linear peptide using a standard solid phase peptide synthesis strategy. The poly-L-lysine with eight units of Peptide 126 or Peptide 127 (see Tables VIa and VIb) were then liberated from the solid phase resin by the HF cleavage procedure, extracted with acetic acid and the octameric peptide lyophilized. The molecular weight of the resulting octameric peptides as determined by SDS-PAGE correlated well with the respective calculated molecular weights of 26,600 and 31,200. Analysis of the HF cleaved octameric Peptide 126 and Peptide 127 both gave broad peaks in C4 reverse phase HPLC.

TABLE VIa

SCHEMATIC DRAWING OF PEPTIDE 126 OCTAMER

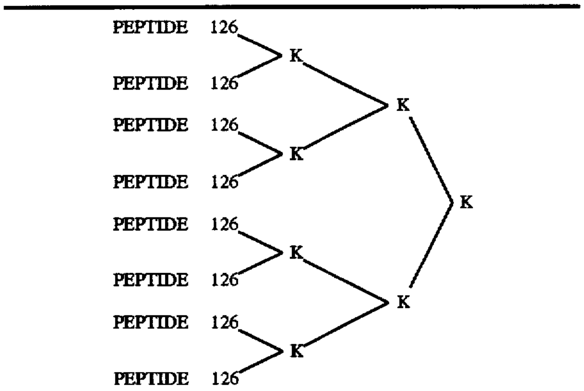

TABLE VIb

SCHEMATIC DRAWING OF PEPTIDE 127 OCTAMER

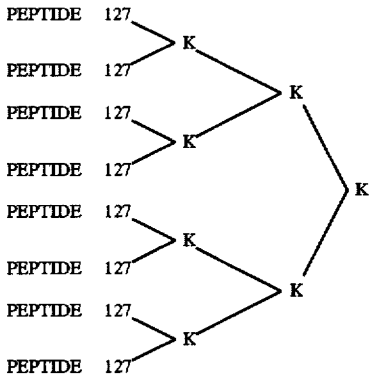

EXAMPLE 7

Guinea Pig Immunization Protocol

Duncan Hartley closed colony random bred female guinea pigs, weighing 400–450 gms, were used in all experiments. Each immunization was administered at the described dosage by subcutaneous and intradermal injection in a volume of 1.0 mL to each member of two guinea pigs over multiple sites. A total of four groups were designed for immunization by: Peptide 126-BSA conjugate, Peptide 127-BSA conjugate, Peptide 126 octamer and Peptide 127 octamer. For the initial immunization, 100 ug peptide conjugate or octamer in 0.5 mL, was mixed with an equal volume of complete Freund's adjuvant (CFA) and 1.0 mL was injected into each animal both subcutaneously and intradermally over multiple sites. After two to three weeks of rest, as a boost, an identical dosage of each of the same immunogen was again injected both subcutaneously and intradermally into each animal, except that incomplete Freund's adjuvant (IFA) was used.

Figure 7:
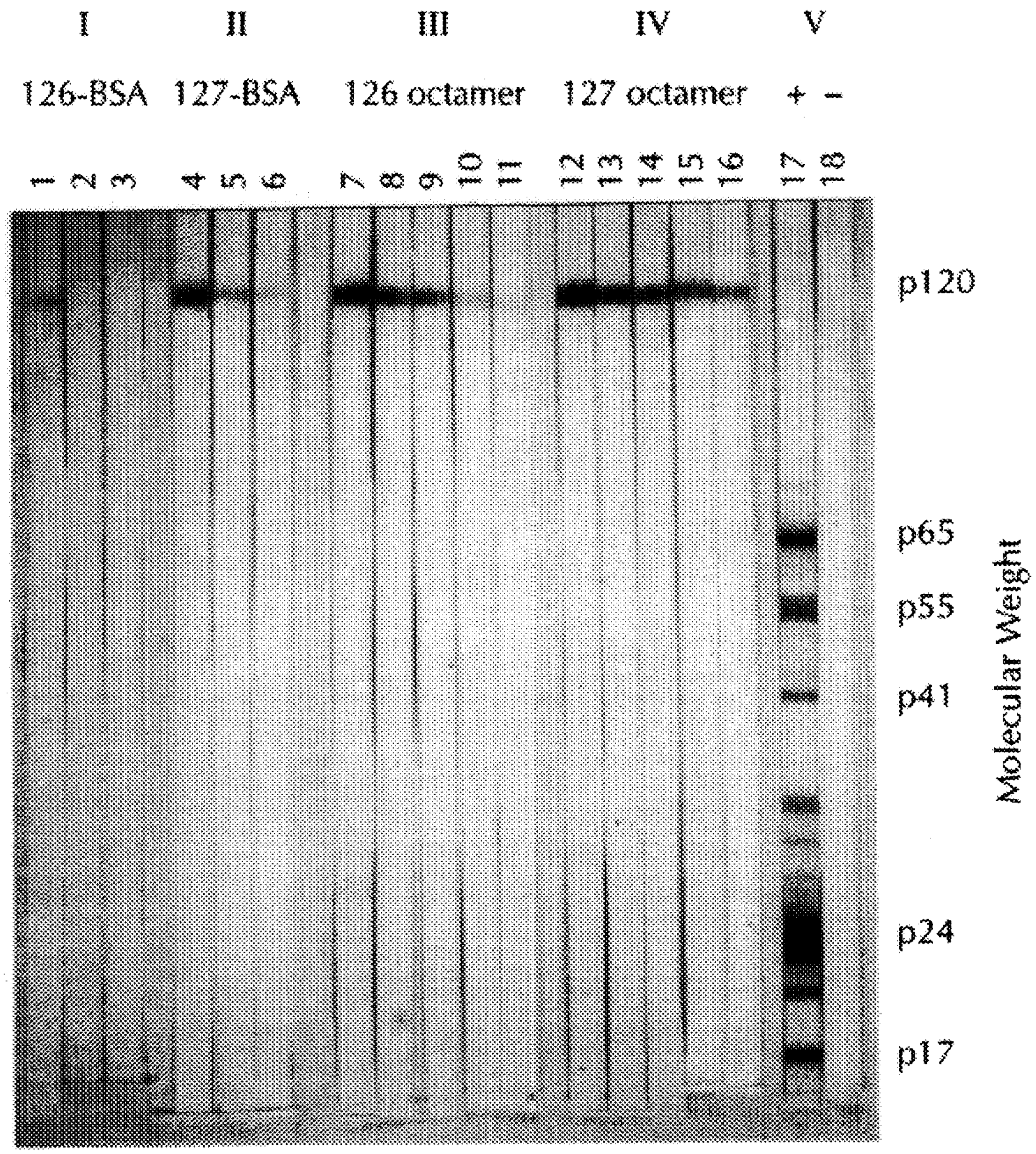
FIG. 7 shows the results of Western Blot Analysis which demonstrates the production of high levels of specific antibodies to gp120 by immunizing guinea pigs with (i) Peptide 126-BSA, with test serum at dilutions of 1:200, 1:1,000, and 1:2,000 (lanes 1–3), (ii) Peptide 127-BSA, with test serum at dilutions of 1:200, 1:1,000 and 1:2,000 (lanes 4–6), (iii) Peptide 126 octamer, with test serum at dilutions of 1:200, 1:1,000, 1:2,000, 1:10,000 and 1:20,000 (lanes 7–11), and (iv) Peptide 127 octamer, with test serum at dilutions of 1:200, 1:1,000, 1:2,000, 1:10,000 and 1:20,000 (lanes 12–16), compared with immunizing a guinea pig with (v) deactivated whole viral lysate, with test serum at dilutions of 1:100 (lane 17) and (vi) a control unimmunized guinea pig, with test serum at a dilution of 1:100 (lane 18). All test sera, except the control sample (vi), were obtained from animals 14 to 17 weeks after initial immunization.

The animals were bled by heart puncture periodically to monitor their serum anti-gp12O titers and subsequent boosts were given every two to six weeks. As shown in FIGS. 6a, 6b, 6c and 6d, Peptide 126-BSA, Peptide 126 octamer, Peptide 127-BSA and Peptide 127 octamer all induced high titer (>1:1000–1:10,000), antibodies to the corresponding immunizing peptide after only one boost. High titers of antibodies cross reactive to the native HIV gp120 protein were also produced as shown by Western Blot analysis. See FIG. 7.

The kinetics of the immune response generated by the specified immunization scheme indicated that effective, sustained level of the high serum antibody titers were elicited during the course of immunization particularly with the octameric form of the peptides. See FIGS. *6a–d* for weeks 10 onwards.

The above results indicate that both Peptide 126 and Peptide 127 represent highly immunogenic epitopes present on the HIV gp120 protein. Sera obtained from guinea pigs previously immunized with the peptide, either in its conjugated or polymeric form, all induced high titers of antibodies to the immunizing peptide and the antibodies elicited were found to be highly crossreactive to the native gp120 as demonstrated by the Western Blot analysis. See FIG. 7.

It is quite remarkable that synthetic peptides representing minute fractions of the external envelope protein of a large virus can be designed to mimic the antigenic/immunogenic sites of the virus to an extent that when used as immunogens, neutralizing or protective antibodies can be elicited (Examples 7, 8, 9 and 10). Furthermore, quantitative EIAs employing these synthetic peptides as the solid phase immunoadsorbent (Example 1) can also be used to detect natural antibodies to gp120 present in HIV infected individuals, to an extent that the presence of neutralizing antibodies to HIV can be predicted by $A_{492nm}$ readings obtained from EIA (Example 3).

EXAMPLE 8

Long-term High Titer HIV-1 Neutralizing Antibodies in Guinea Pigs Elicited by Peptide 127 Octamer Observations on the antibody response of the guinea pigs to Peptide 127 octamer following the initial immunization schedule as described in Example 7 were extended for a total of 3½ years. The immunogenicity of Peptide 127 octamer was compared to that of monomeric Peptide 127 coupled to BSA via conventional glutaraldehyde cross-linking (Peptide 127-BSA) and to that of whole inactivated HIV. EIA titers were determined on microtiter plates coated with 5 μg/mL monomeric Peptide 127 according to the procedure described in Example 1 except that peroxidase conjugated goat anti-guinea pig IgG was used as the tracer. The EIA titers are expressed as the reciprocal serum dilution at which $A_{492nm}$ was 1.0.

Table VII shows the reactivities of sera from immunized guinea pigs. Guinea pigs (two per immunogen) were immunized with HIV lysate, Peptide 127-BSA and Peptide 127 octamer and bled as described in Example 7 and shown in FIG. 8. Every value except at 165 wpi (weeks post initial immunization) were for sera pooled from two animals. The values at 165 wpi were from the antiserum of one surviving animal which was the lower responder of the pair. EIA titers (anti-peptide 127 and anti-HIV) were determined as in Example 8 and expressed as the logarithms of the end point serum dilutions to anti-Peptide 127, or to HIV-1 lysate. Western blot titers to gp120 of isolate $HIV\text{-}1_{IIIB}$, determined as shown in FIG. 9, refer to logarithms of the end point dilutions that gave consistent, detectable gp120 signals. Neutralization antibody titers, obtained by immunofluorescence detection of p24 of HIV clone HX10 (IIIB) or clone RFII, refer to the end point dilutions that caused complete inhibition of p24 expression at 2 weeks of $10\times TCID_{50}$ except that at 165 wpi, the challenge dose was $100\times TCID_{50}$. Fusion inhibition, scored as syncytial foci (SFU), was performed in microtiter wells by mixing uninfected CEM cells with CEM cells infected with $HIV\text{-}1_{IIIB}$ or $HIV\text{-}1_{RFII}$ with or without antisera which had been diluted 1:20.

TABLE VII

Activity of Immune Sera to Peptide 127 and gp120

| Antisera | Titer: EIA ($Log_{10}$) (Anti-peptide 127) | Titer: Western Blot ($Log_{10}$) (Anti-gp120) | Neutralization Antibody Titer: $HIV\text{-}1_{IIIB}$ | Neutralization Antibody Titer: $HIV\text{-}1_{RFII}$ |
|---|---|---|---|---|
| Preimmune | <1 | <1 | <4 | <4 |
| Anti-HIV | | | | |
| 38 wpi | 4[a] | <2 | <2 | <4 |
| Anti-p127-BSA | | | | |
| 5 wpi | 4 | 2.5 | 16 | <4 |
| 16 wpi | 3.5 | 3.5 | 256 | <4 |
| 38 wpi | 3.0 | 3.0 | 128 | <4 |
| 45 wpi | 2.8 | 3.0 | 64 | <4 |
| 75 wpi | 2.8 | 2.8 | 64 | <4 |
| Anti-octamer p127 | | | | |
| 6 wpi | 4.5 | 2.8 | <4 | <4 |
| 14 wpi | 4.0 | 4.0 | 256[b] | <4 |
| 37 wpi | 4.5 | 4.5 | 1024 | <4 |
| 48 wpi | 5.0 | 5.0 | 4096 | <4 |
| 165 wpi[c] | 5.0 | 5.5 | ≧19683[d] | 64 |

[a]Anti-HIV measured from pooled sera taken at 38 weeks after three immunizations of 2 guinea pigs, at 50 ug per dose, in complete/incomplete Freund's adjuvants with inactivated $HIV\text{-}1_{IIIB}$.
[b]These sera were also assayed in a fusion inhibition assay and showed 90% inhibition against $HIV\text{-}1_{IIIB}$, but no detectable inhibition against $HIV\text{-}1_{RFII}$.
[c]Serum was obtained from surviving animal which was the lower responder of the pair. This serum also cross-neutralized $HIV\text{-}1_{MN}$ isolate at a titer of 1:1024.
[d]Challenge dose was 100 times $ICID_{50}$.

Figure 8:
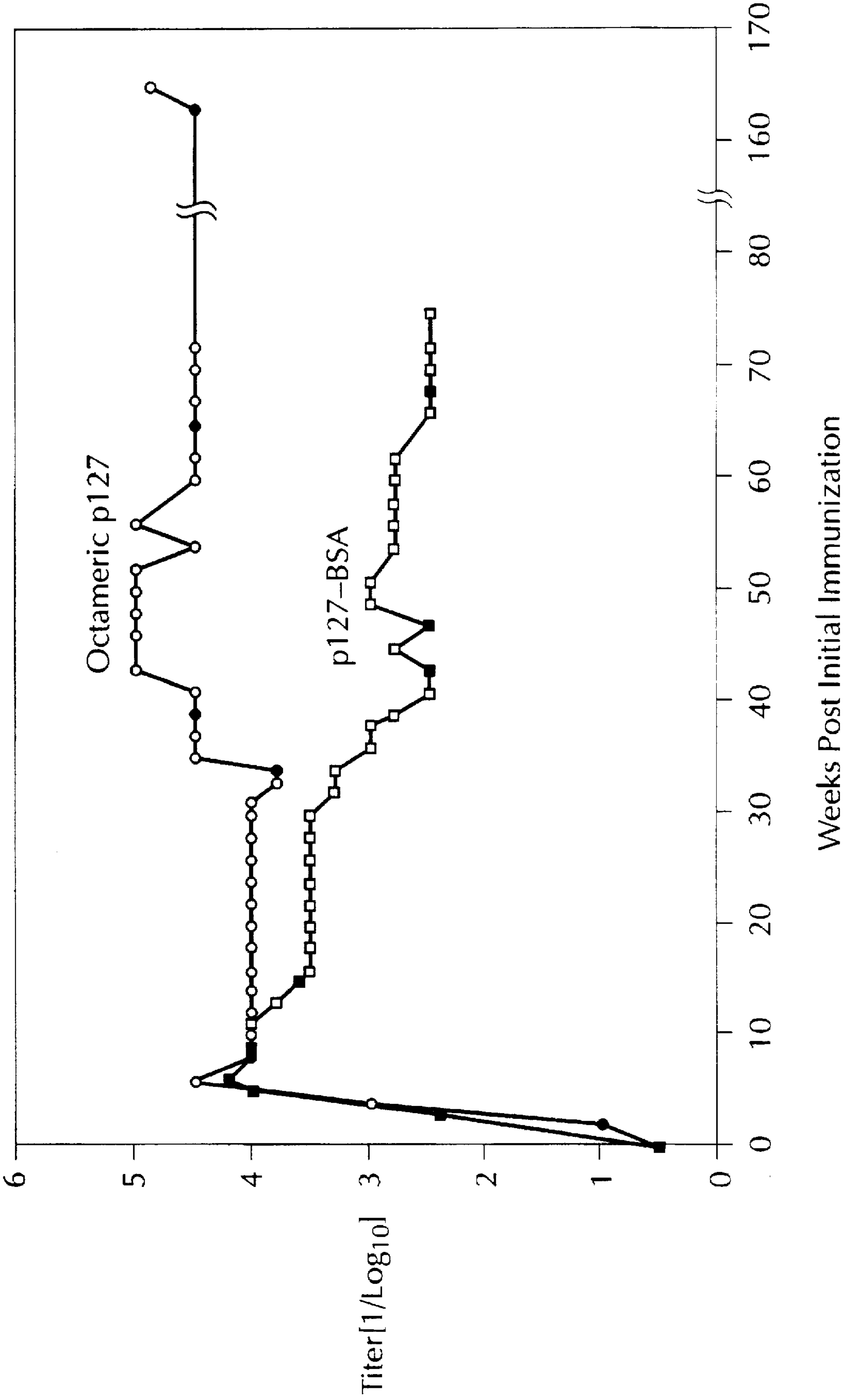
FIG. 8 shows the kinetics of antibody response to peptide 127 over a 3½ year period in guinea pigs previously immunized by peptide 127 derived immunogens. The animals were immunized and boosted initially as described in Example 7. Subsequent boosts were given at the points shown by solid symbols. Guinea pig no. 84, immunized with octameric peptide 127 (o,●), and guinea pig no. 43 was immunized with peptide 127-BSA (□,■). The animals were periodically bled as shown.
Figure 9A:
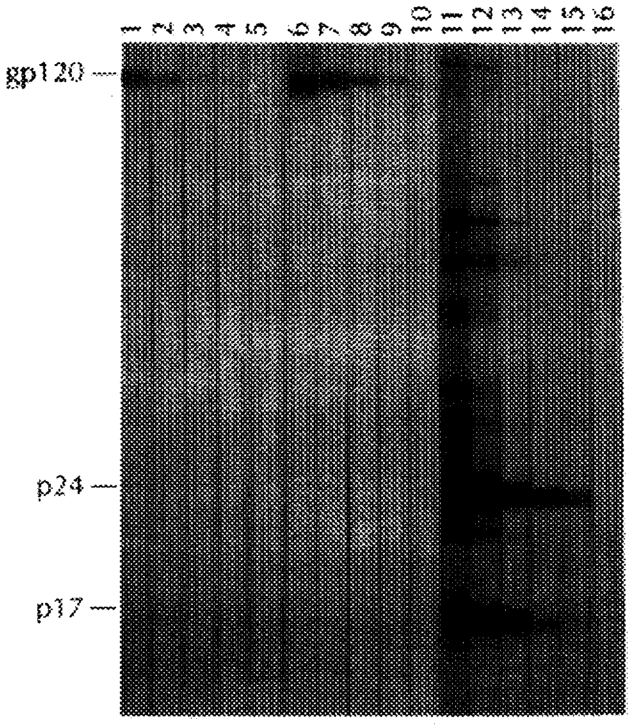
FIG. 9 shows the reactivity of guinea pig antisera to HIV gp120, detected by end point dilution titers on Western blot strips. In A, each test serum was titered on five strips at dilutions of 1:100, 1:500, 1:2500, 1:12,500, and 1:62,500; Strips 1–5, guinea pig antiserum to peptide 127-BSA at 38 weeks post-immunization; strips 6–10, antiserum to peptide 127 octamer at 37 weeks; strips 11–15, anti-HIV (deactivated whole viral lysate) guinea pig serum at 38 weeks; strip 16, normal guinea pig serum diluted 1:100. In B, guinea pig no.84 antiserum to peptide 127 octamer at week 165 (3½ years): Western blot strips 1–6 are titered with antiserum serially diluted 1:100, 1:500, 1:7500, 1:12,500, 1:62,500, 1:312,500, respectively; strip 7, normal guinea pig serum diluted 1:100.
Figure 9B:
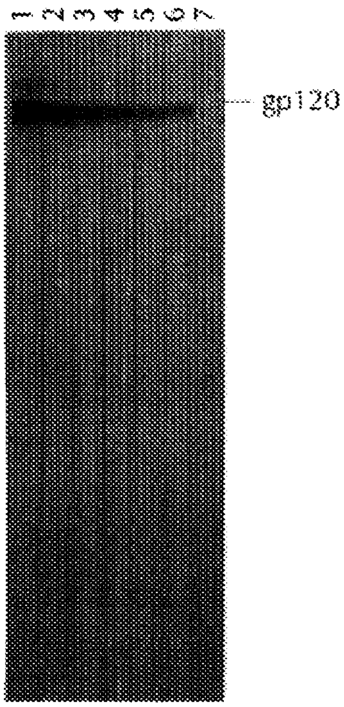

As shown in FIG. 8 and Table VII, both Peptide 127-BSA and Peptide 127 octamer induced specific and high titer (>1:1000–1:10,000) anti-peptide antibodies after one boost (3 weeks after initial immunization). Both peptide immunogens elicited antibodies effective in the neutralization and fusion inhibition of HIV (Table VII). These activities also correlated with the EIA and anti-gp120 titers (Table VII, FIGS. 8,9).

The Peptide 127-BSA immunogen elicited neutralizing antibodies slightly earlier than the Peptide 127 octamer, beginning the 5th week after the initial immunization, with neutralization titers in the range of 1:16–1:256 (Table VII) However, the Peptide 127 octamer immunogen was more effective over time in boosting the animals' neutralizing antibodies (Table VII). In animals immunized with the Peptide 127 octamer, neutralizing antibodies were detected by the 14th week. By week 37, these animals consistently gave 100× to 1000× higher anti-gp120 titers than animals receiving the inactivated HIV lysate (Table VII). After week 37, the Peptide 127 octamer immunized animals also displayed stronger secondary immune responses to boosting than did those guinea pigs immunized with Peptide 127-BSA (FIG. 8). Once developed, such high levels of anti-octamer neutralizing antibodies were detected throughout the 3½ year period of the study (Table VII, FIG. 8).

Beginning at weeks 5–6, the anti-peptide sera were found to be reactive with native HIV-$1_{IIIB}$ gp120 protein, as determined by immunoblot analysis (Table VII). The gp120-specific titers of the anti-peptide sera gradually increased to equal the peptide 127 antibody titers by weeks 14–16 (Table VII). This indicates an improvement in the quality of the immune response whereby low affinity anti-peptide antibodies gradually are replaced by antibodies with higher affinities for gp120. The cross-reactivities of Peptide 127-BSA antisera to gp120 reached levels 10× higher than those induced by inactivated HIV lysate by week 38 (Table VII, FIG. 9, A). The disparity between the gp120-directed response induced by Peptide 127 octamer and the response induced by inactivated HIV lysate was even greater at this time. The titers of anti-octamer sera to gp12o were higher by factors of 100× to 1000× than those elicited by inactivated HIV lysate (Table VII and FIG. 9, A). Apparently, the antibody response to inactivated HIV lysate was largely directed toward the more immunodominant p24 and p17 HIV antigens rather than to gp120 (FIG. 9, A). After a resting period from 80 to 163 wpi, the serological reactivity to Peptide 127 and gp120 of one of the Peptide 127 octameric immunized animal was reexamined. By 163 wpi, the guinea pig was found to have maintained an appreciable antibody titer to Peptide 127 of 4.5 ($1/\log_{10}$) (FIG. 8), and by 165 wpi, showed a good anamnestic response raising the titer to 4.9 ($1/\log_{10}$) (FIG. 8), a strong gp120-specific antibody response of 5.5 ($1/\log_{10}$) (FIG. 9, B), and to have attained a very high neutralization antibody titer≧1:19,683 against $HIV_{IIIB}$, as well as cross-neutralizing activity to HIV-$1_{RFII}$ of 1:64 (Table VII) and to the more prevalent HIV-$1_{MN}$ type of 1:1024 (Table VII, legend c). It should be noted that the increase in neutralizing antibody titer suggests a continued improvement in the quality of the antibody response that persisted. The neutralizing activity induced by Peptide 127 octamer correlated with the high titers obtained for peptide 127 or gp120 binding, a situation similar to that observed in Example 3.

Octameric peptides, synthesized as analogues of Peptide 127, were also evaluated to determine the length of peptide chain that confers the best antigenic presentation for the neutralizing epitope, also termed the principal neutralizing determinant (PND). As shown in Table VIII, the length of the peptide chain in an octameric structure was proportional to its ability to elicit anti-peptide antibodies. However, only when the epitope was presented in a loop structure with residues Gly-Pro-Gly-Arg (SEQ NO. 22) located in a more central position, did the peptides elicit native gp120 reactive antibodies (e.g. Peptides 127g', 127h' and 127). An appreciable neutralization titer could be demonstrated only in response to Peptide 127 octamer, and not Peptide 127g' octamer nor Peptide 127h' octamer. This suggests that the first thirteen amino acids in the sequence Gln-Ser-Val-Glu-Ile-Asn-Cys-Thr-Arg-Pro-Asn-Asn-Asn (amino acids 297–309 of HIV-$1_{IIIB}$ gp120) (SEQ NO. 23), corresponding to the amino terminal portion of the loop, enhance the biologically relevant antigenicity of that determinant. A five residue extension of the sequence on the carboxy terminal of Peptide 127 yielded equivalent antigenicity, i.e. led to no further improvement.

The positions that affect the antigenicity of Peptide 127 octamer were more precisely localized by measurement of relative binding affinities of a set of nested peptides for the antibodies in guinea pig anti-Peptide 127 octamer sera. Relative binding affinities were equated to the antigen-limiting concentrations of peptide antigens, as determined on an antigen-limited EIA shown in Table IX. In these antigen-limited EIAs, Peptide 127 analogues: 267a, 267b, 267c and 267d, were coated at a decreasing concentration of 5 μg/mL, 1 μg/mL, 0.2 or 0.4 μg/mL, according to the procedure described in Example 1. The concentration in an antigen-limited EIA as shown in Table IX was the peptide coating concentration at which a $10^{-2}$ dilution of guinea pig antiserum gave an EIA reading of $A_{492nm}=1$. This method provides a simple alternative for the measurement of relative antibody binding affinities. As shown in Table IX, by week 14 wpi, Peptide 267c had the strongest avidity of the nested peptides for the antibodies to Peptide 127 octamer. This peptide contains the central Gly-Pro-Gly-Arg (SEQ NO. 22) sequence of the loop. The serum containing antibodies to Peptide 127 octamer was found to be devoid of high affinity binding activity to Peptide 267b throughout the entire period of this study, but it displayed appreciable avidity for the more distal Peptide 267a. By 165 wpi, the avidity of antibodies to Peptide 267a exceeded that of antibodies to Peptide 267d. This was consistent with the contribution of the group Gln-Ser-Val-Glu-Ile-Asn (SEQ NO. 24) to the overall immunogenicity of Peptide 127 octamer (Table VIII). The antibody binding affinities and EIA titers to the small nested peptides were consistently lower than those of Peptide 127 (Table IX), and they did not display increases with time comparable to the large increases in the anti-gp120 titers and in the neutralization antibody titers of anti-Peptide 127 octamer sera measured during this period (Table VII, FIGS. 8, 9, A & B). This result suggests that improvements in the quality of the antibodies were in response to native conformational epitopes on the branched synthetic antigen rather than solely in response to linear epitopes.

Of practical importance is that when alum, an adjuvant more appropriate for human use, was substituted for Freund's adjuvant in guinea pig immunizations, the antibody response as measured by EIA titers was only slightly reduced. For example, an analogue of Peptide 127 with its amino acid sequence derived from the most prevalent HIV-$1_{MN}$ type (Example 9, Table X) were $1/\log_{10}$ 4.5 to 5 with Freund's adjuvant and $1/\log_{10}$ 3.5 to 4.0 with 2% alum.

In summary, when Peptide 127 was synthesized as an octameric peptide by attaching eight copies to a branching heptalysyl core and used as an immunogen, it elicited high titer gp120 binding neutralizing antibodies in guinea pigs with quality far superior to those of the antisera generated by either Peptide 127-BSA conjugate or deactivated HIV viral lysate. The anti-Peptide 127 octamer guinea pig sera displayed persistent neutralizing antibody titers much higher than ever seen before in animals or in man, to the HIV-$1_{IIIB}$ isolate, as well as measurable cross-serotype neutralizing activities. The antibodies were predominantly of high affinity and were associated with a good memory response.

TABLE VIII

Relative Immunogenicity of Octameric Peptide 127 Analogues

| Peptide Code | Amino Acid Sequence | EIA Titers to Peptide 127 ($Log_{10}$) | EIA Titers to gp120 ($Log_{10}$) | Neutralization Antibody Titers |
|---|---|---|---|---|
| 127a' (SEQ NO. 25) | ThrArgLysSerIleArgIleGlnArgGlyProGlyArg | 2.8 | <1 | <4 |
| 127b' (SEQ NO. 26) | CysThrArgProAsnAsnAsnThrArgLysSerIleArgIleGlnArgGlyProGlyArg | 3.8 | <1 | <4 |
| 127g' (SEQ NO. 27) | ArgIleGlnArgGlyProGlyArgAlaPheValThrIleGlyLys | 3.5 | 2.5 | <4 |
| 127h' (SEQ NO. 28) | ThrArgLysSerIleArgIleGlnArgGlyProGlyArgAlaPheValThrIleGlyLys | 4.0 | 3.5 | 20 |
| 127 (SEQ NO. 11) | GlnSerValGluIleAsnCysThrArgProAsnAsnAsnThrArgLysSerIleArgIle GlnArgGlyProGlyArgAlaPheValThrIleGlyLys | 4.5 | 4.5 | 512 |

TABLE IX

Relative Antibody Binding Affinities and Immunogenicities of Analogues of Octameric Peptide 127.

| | | Concentration* in antigen-Limited EIA titers (µg/mL) | | | |
|---|---|---|---|---|---|
| Peptide Code | Amino Acid Sequence | 6 wpi | 14 wpi | 37 wpi | 165 wpi |
| 267a (SEQ NO. 23) | GlnSerValGluIleAsnCysThrArgProAsnAsnAsn | 1.0 (300)+ | 0.2–1.0 (300)+ | 1.0–5.0 (1000)+ | 0.2–1.0 (300)+ |
| 267b (SEQ NO. 29) | CysThrArgProAsnAsnAsnThrArgLysSerIleArg | >5 (10) | 5 (100) | 5 (30) | >5 (<10) |
| 267c (SEQ NO. 25) | ThrArgLysSerIleArgIleGlnArgGlyProGlyArg | 0.04–0.2 (3000) | <0.04 ($1 \times 10^4$) | 0.2 (300) | 0.04 (1000) |
| 267d (SEQ NO. 30) | ArgGlyProGlyArgAlaPheValThrIleGlyLys | 1.0–5.0 (30) | 0.2 ($1 \times 10^4$) | 0.2–1.0 (300) | 1.0–5.0 (300) |
| 127 (SEQ NO. 11) | GlnSerValGluIleAsnCysThrArgProAsnAsnAsnThr ArgLysSerIleArgIleGlnArgGlyProGlyArgAlaPhe ValThrIleGlyLys | 0.04–0.2 ($3 \times 10^4$) | 0.008–0.04 ($1 \times 10^4$) | 0.04–0.2 ($3 \times 10^4$) | 0.008 ($1 \times 10^5$) |

*The antigen-limited concentration (µg/mL) was the peptide coating concentration at which at $10^{-2}$ dilution of guinea pig antioctamer serum gave a signal of $A_{492nm}$#1.
+EIA titers, shown in parentheses, were determined as in Example 8, at a peptide coating concentration of 5.0 µg/mL for solid phase antigen.

EXAMPLE 9

Peptide 127 Analogue

An analogue of Peptide 127 is shown here to have similarly useful immunogenic properties, being effective in eliciting the production of neutralizing antibodies against HIV-1.

The peptide selected for this demonstration, a sequence taken from the HIV-$1_{MN}$ isolate, is analogous to that segment of HIV-$1_{IIIB}$ isolate BH10 of Peptide 127. The MN analogue was selected because the MN isolate of HIV-1 and strains with similar sequences are responsible for the majority of infections in North America. The analogous MN peptide, designated as peptide 200, has the amino acid sequence Glu-Ser-Val-Gln-Ile-Asn-Cys-Thr-Arg-Pro-Asn-Tyr-Asn-Lys-Arg-Lys-Arg-Ile-His-Ile-Gly-Pro-Gly-Arg-Ala-Phe-Tyr-Thr-Thr-Lys-Asn-Ile-Ile-Gly. See Table IIb.

The HIV-$1_{MN}$ peptide, designated Peptide 200, was prepared as an octameric immunogen, i.e. Peptide 200 octamer, and its immunogenicity established by testing in pairs of Duncan Hartley guinea pigs. Guinea pigs were immunized subcutaneously at week 0, and boosted at 3, and 6 wpi as in Example 7. Two guinea pigs were immunized with 100 µg/dose using CFA/IFA for adjuvants, as in Example 7. Three other pairs received immunizations of Peptide 200-PBS solutions emulsified into equal volumes of 2% alum, the adjuvant approved for use in humans. Each of these three pairs was given respectively 100, 20, or 4 µg doses of Peptide 200 octamer with alum as adjuvant. The immune response generated is presented in Table X, measured by Peptide 200 EIA. An appreciable anti-peptide response was observed by 3 wpi and all animals reached plateaus for antibody titers by 12 wpi. The final titers generated with the two adjuvants were $1/\log_{10}$ 4.8 for CFA/IFA and $1/\log_{10}$ 3.8 for all 3 alum emulsions. The strong response to the alum formulations did not vary within the immunogen dose range of 4 to 100 µg, showing the efficacy of Peptide 200 octamer as an immunogen. High anti-Peptide 200 could be correlated to significant neutralizing activity against HIV-$1_{MN}$. The antisera induced by the CFA/IFA emulsion had a very high NA titer to $HIV_{MN}$ of 1:8192 at 54 wpi as well as significant cross-neutralizing activity to $HIV_{IIIB}$, 1:256. NA titers were measured by the fusion inhibition NA bioassay, scoring syncytial foci. See Example 10 for procedure.

TABLE X

Immunogen Dosage Study With Octameric Peptide 200

| | 1/Log10[Ab Titer] | | | |
|---|---|---|---|---|
| | CFA/ICFA | ALUM | | |
| Time Of Bleed | 100 µg | 100 µg | 20 µg | 4 µg |
| 0* | 0 | 0 | 0 | 0 |
| 3* | 5.3 | 4.3 | 4 | 3.5 |
| 6* | 5 | 4 | 4.3 | 4 |
| 9 | 4.8 | 3.8 | 3.8 | 4.2 |

TABLE X-continued

| Immunogen Dosage Study With Octameric Peptide 200 | | | | |
|---|---|---|---|---|
| | 1/Log$_{10}$[Ab Titer] | | | |
| | CFA/ICFA | ALUM | | |
| Time Of Bleed | 100 μg | 100 μg | 20 μg | 4 μg |
| 12 | 4.8 | 3.8 | 3.8 | 3.8 |
| 15 | 4.8 | 3.8 | 3.8 | 3.8 |
| 18 | 4.8 | 3.8 | 4 | 4 |
| 21 | 4.8 | 3.8 | 3.8 | 3.8 |
| 51* | 4.8 | 3.8 | 3.8 | 3.8 |
| 54 | >5 | >4 | >4 | >4 |

*: Immunization and boost

EXAMPLE 10

Use of a Mixture of peptide 127 Analogues to Achieve a Broad Neutralizing Antibody Response Pairs of guinea pigs were immunized with a mixture of octameric peptides corresponding to the analogues of Peptide 127 with sequences taken from HIV-1 isolates IIIB, MN, SC, SF2, WMJ2, and RFII. See Table IIb. The peptides were designated Peptide 127, Peptide 200, Peptide 281, Peptide 283, Peptide 282, and Peptide 280, respectively. The octameric form of each of the peptides synthesized according to the procedure described in Example 6 was used as the immunogen.

Two pairs of guinea pigs were immunized with a dose containing a mixture of six octameric peptides at week 0 and boosted at 3, and 6 wpi, as in Example 7. The doses of antigen mixture contained 4 μg of each immunogen (i.e., 24 μg total). One pair of the animals was inoculated using the Freund's adjuvant protocol (CFA/IFA), the other pair was inoculated using the 2% alum adjuvant protocol. The EIA titers were determined at 3 wpi and 6 wpi after the first boost for each peptide, as in Example 7. The EIA titers were >5 (l/log$_{10}$) to all of the peptides in antisera raised to the octameric peptide mixture with CFA/IFA, and EIA titers were >4–5 (l/log$_{10}$) raised to the octameric peptide mixture with alum. A significant antibody response to a wide selection of HIV-1 strains had been stimulated, even in this early bleed sera. The high anti-peptide titers generated in response to all six peptides at 6 wpi is evidence showing the broad and potent immunogenicity of the octameric mixture. The high EIA titers were representative of neutralizing activity for a wide variety of HIV-1 isolates/strains.

NA titers for HIV-I$_{IIIB}$ and HIV-1$_{MN}$ were determined by the syncytium inhibition NA assay. Briefly, neutralization of 50 syncytia forming units (SFU) of HIV-1$_{IIIB}$ were measured with serially diluted guinea pig antisera ranging from 1:16 to 1:16,384 and expressed as surviving fraction of input virus ($V_o/V_n$). Virus and sera mixtures, preincubated for 45 min. at 4° C. and 15 min. at 20° C., were incubated for 2 hrs. with HT4-6C Hela $CD_4^+$ cells (cells pretreated with DEAE-dextran) seeded 24 hrs previously into 48-well plates at a density of $4\times10^4$ cells/well. Neutralization plates were incubated for 5 days, fixed in methanol, stained and scored. Representative results obtained with serum from a guinea pig immunized with this mixture containing Peptide 127 octamer and the octameric forms of its five analogues using alum as the adjuvant are shown in Table XI. The early bleed serum from one of the immunized animals already displayed neutralization activity at an impressive level for HIV-1$_{MN}$ (>1:4096), and to a less impressive but still significant level for HIV-1$_{IIIB}$ (>1:256). The broad serum neutralization activity is evidence for the ability of octameric peptide mixtures to induce a broadly protective immune response in immunized animals.

TABLE XI

| Titration of Serum Neutralization Antibodies of Guinea Pigs At 6 wpi with Mixture of Octameric Peptide 127 Analogues | | |
|---|---|---|
| | Vo/Vn | |
| Serum Dilution | HIV-1$_{MN}$ | HIV-1$_{IIIB}$ |
| 1:65,536 | 1.00 | 1.00 |
| 1:16,384 | 0.75 | 1.00 |
| 1: 4,096 | 0.20* | 1.10 |
| 1: 1,024 | 0.35* | *0.70 |
| 1: 256 | 0.10* | *0.20 |
| 1: 16 | 0.20* | *0.10 |
| 1: 4 | 0.10* | *0.10 |

*: Significant Neutralization of HIV replication

Vo/Vn: Fraction of surviving input virus (50 SFU). Neutralization titer is the serum dilution at which Vo/Vn is less than 0.5.

I claim:

1. A composition comprising a peptide selected from the group consisting of:

Gln-Ser-Val-Glu-Ile-Asn-Cys-Thr-Arg-Pro-Asn-Asn-Asn-Thr-Arg-Lys-Ser-Ile-Arg-Ile-Gln-Arg-Gly-Pro-Gly-Arg-Ala-Phe-Val-Thr-Ile-Gly-Lys-X Peptide 127 (SEQ ID NO: 11), wherein X is —OH or —$NH_2$;

a peptide from a strain/isolate of HIV corresponding to Peptide 127;

a conjugate of Peptide 127;

a conjugate of a peptide from a strain/isolate of HIV corresponding to Peptide 127;

a poly-L-lysine polymer of Peptide 127;

a poly-L-lysine polymer of a peptide from a strain/isolate of HIV corresponding to Peptide 127; and a mixture thereof.

2. The composition of claim 1, wherein the peptide is selected from the group consisting of:

(i) Ala-Ser-Val-Gln-Ile-Asn-Cys-Thr-Arg-Pro-Asn-Asn-Thr-Arg-Lys-Ser-Ile-Thr-Lys-Gly-Pro-Gly-Arr-Val-Ile-Thr-Ala-Thr-Gly-Gln-X Peptide $127_{RF}$ (SEQ ID NO: 18);

(ii) Glu-Ser-Val-Glu-Ile-Asn-Cys-Thr-Arg-Pro-Tyr-Asn-Asn-Val-Arg-Arg-Ser-Leu-Ser-Ile-Gly-Pro-Gly-Arg-Ala-Phe-Arg-Thr-Arg-Glu-Ile-X Peptide $127_{WMJ-2}$ (SEQ ID NO: 15);

(iii) Glu-Ser-Val-Ala-Ile-Asn-Cys-Thr-Arg-Pro-Asn-Asn-Thr-Arg-Lys-Ser-Ile-Arg-Tyr-Gln-Arg-Gly-Pro-Gly-Arg-Ala-Phe-His-Thr-Thr-Gly-Arg-X Peptide $127_{SF2}$ (SEQ ID NO: 13);

(iv) Lys-Ser-Val-Glu-Ile-Asn-Cys-Thr-Arg-Pro-Asn-Asn-Asn-Thr-Lys-Lys-Gly-Ile-Ala-Ile-Gly-Pro-Gly-Arg-Thr-Leu-Tyr-Ala-Arg-Glu-Lys-X Peptide $127_{NY5}$ (SEQ ID NO: 17); and (v) Glu-Thr-Val-Thr-Ile-Asn-Cys-Thr-Arg-Pro-Gly-Asn-Asn-Thr-Arg-Arg-Gly-Ile-His-Phe-Gly-Pro-Gly-Gln-Ala-Leu-Tyr-Thr-Thr-Gly-Ile-X Peptide $127_{MAL}$ (SEQ ID NO:19)

wherein X is —OH or —$NH_2$;

a poly-L-lysine polymer of any one of (i)-(v);

a conjugate of any one of (i)-(v) and a mixture thereof.

3. The composition according to claim 2 wherein the peptide is: Ala-Ser-Val-Gln-Ile-Asn-Cys-Thr-Arg-Pro-Asn-Asn-Thr-Arg-Lys-Ser-Ile-Thr-Lys-Gly-Pro-Gly-Arg-Val-Ile-Tyr-Ala-Thr-Gly-Gln-X Peptide $127_{RF}$ (SEQ ID NO: 18);

wherein X is —OH or —$NH_2$, or conjugate thereof.

4. The composition according to claim 2 wherein the peptide is: Glu-Ser-Val-Glu-Ile-Asn-Cys-Thr-Arg-Prg-Tyr-Asn-Val-Arg-Arg-Ser-Leu-Ser-Ile-Gly-Pro-Gly-Arg-Ala-Phe-Arg-Thr-Arg-Glu-X Peptide $127_{WMJ-2}$ (SEQ ID NO: 15)

wherein X is —OH or —$NH_2$, or a conjugate thereof.

5. The composition according to claim 2, wherein the peptide is: Glu-Ser-Val-Ala-Ile-Asn-Cys-Thr-Arg-Pro-Asn-Asn-Thr-Arg-Lys-Ser-Ile-Tyr-Ile-Gly-Pro-Gly-Arg-Ala-Phe-His-Thr-Thr-Gly-Arg-X Peptide $127_{SF2}$ (SEQ ID NO: 13);

wherein X is —OH or —$NH_2$, or a conjugate thereof.

6. The composition according to claim 2 wherein the peptide is: Lys-Ser-Val-Glu-Ile-Asn-Cys-Thr-Arg-Pro-Asn-Asn-Asn-Thr-Lys-Lys-Gly-Ile-Ala-Ile-Gly-Pro-Gly-Arg-Thr-Leu-Tyr-Ala-Arg-Glu-Lys Peptide $127_{NY5}$ (SEQ ID NO: 17).

7. The composition according to claim 2 wherein the peptide is: Glu-Thr-Val-Thr-Ile-Asn-Cys-Thr-Arg-Pro-Gly- Asn-Asn-Thr-Arg-Arg-Gly-Ile-His-Phe-Gly-Pro-Gly-Gln-Ala-Leu-Tyr-Thr-Thr-Gly-Ile Peptide $127_{MAL}$ (SEQ ID NO: 19).

8. The composition according to claim 1 wherein the conjugate is a protein having a molecular weight of at least 5,000.

9. The composition of claim 8 wherein the protein is serum albumin.

10. A method for detecting antibodies to HIV and neutralizing antibodies to HIV-gp120 in an immunoassay by using as an immunosorbent the composition of claim 1.

11. A method for detecting antibodies to HIV and neutralizing antibodies to HIV-gp120 in an immunoassay by using as an immunosorbent the composition of claim 2.

12. A method for detecting antibodies to HIV and neutralizing antibodies to HIV-gp120 in an immunoassay by using as an immunosorbent the composition of claim 3.

13. A method for detecting antibodies to HIV and neutralizing antibodies to HIV-gp120 in an immunoassay by using as an immunosorbent the composition of claim 4.

14. A method for detecting antibodies to HIV and neutralizing antibodies to HIV-gp120 in an immunoassay by using as an immunosorbent the composition of claim 5.

15. A method for detecting antibodies to HIV and neutralizing antibodies to HIV-gp120 in an immunoassay by using as an immunosorbent the composition of claim 6.

16. A method for detecting antibodies to HIV and neutralizing antibodies to HIV-gp120 in an immunoassay by using as an immunosorbent the composition of claim 7.

17. A method of eliciting neutralizing antibodies to HIV in a mammal by introducing into the mammal the composition of claim 1.

18. A method of eliciting neutralizing antibodies to HIV in a mammal by introducing into the mammal the composition of claim 2.

19. A method of eliciting neutralizing antibodies to HIV in a mammal by introducing into the mammal the composition of claim 3.

20. A method of eliciting neutralizing antibodies to HIV in a mammal by introducing into the mammal the composition of claim 4.

21. A method of eliciting neutralizing antibodies to HIV in a mammal by introducing into the mammal the composition of claim 5.

22. A method of eliciting neutralizing antibodies to HIV in a mammal by introducing into the mammal the composition of claim 1.

23. A method of eliciting neutralizing antibodies to HIV in a mammal by introducing into the mammal the composition of claim 7.

* * * * *

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
( A ) LENGTH: 28 amino acids
( B ) TYPE: Amino acid
( C ) STRANDEDNESS:
( D ) TOPOLOGY: Unknown ( i i ) MOLECULE TYPE: Peptide -continued ( i i i ) HYPOTHETICAL: No ( i v ) ANTI-SENSE: No ( v ) FRAGMENT TYPE:

( v i ) ORIGINAL SOURCE:
( A ) ORGANISM:
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( v i i ) IMMEDIATE SOURCE:
( A ) LIBRARY:
( B ) CLONE:

( v i i i ) POSITION IN GENOME:
( A ) CHROMOSOME/SEGMENT:
( B ) MAP POSITION:
( C ) UNITS:

( i x ) FEATURE:
( A ) NAME/KEY:
( B ) LOCATION:
( C ) IDENTIFICATION METHOD:
( D ) OTHER INFORMATION:

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION:SEQ ID NO: 1:

```
Cys Arg Ile Lys Gln Ile Ile Asn Met Trp Gln Glu Val Gly Lys
1               5                   10                  15

Ala Met Tyr Ala Pro Pro Ile Ser Gly Gln Ile Arg Cys
20                  25
```

( 2 ) INFORMATION FOR SEQ ID NO: 2:

( i ) SEQUENCE CHARACTERISTICS:
( A ) LENGTH: 28 amino acids
( B ) TYPE: Amino acid
( C ) STRANDEDNESS:
( D ) TOPOLOGY: Unknown ( x i ) SEQUENCE DESCRIPTION:SEQ ID NO: 2:

```
Cys Arg Ile Lys Gln Phe Ile Asn Met Trp Gln Glu Val Gly Lys
1               5                   10                  15

Ala Met Tyr Ala Pro Pro Ile Ser Gly Gln Ile Arg Cys
20                  25
```

( 2 ) INFORMATION FOR SEQ ID NO: 3:

( i ) SEQUENCE CHARACTERISTICS:
( A ) LENGTH: 28 amino acids
( B ) TYPE: Amino acid
( C ) STRANDEDNESS:
( D ) TOPOLOGY: Unknown -continued ( x i ) SEQUENCE DESCRIPTION:SEQ ID NO: 3:

Cys Arg Ile Lys Gln Ile Ile Asn Met Trp Gln Lys Val Gly Lys
1 5 10 15

Ala Met Tyr Ala Pro Pro Ile Ser Gly Gln Ile Arg Cys
20 25

( 2 ) INFORMATION FOR SEQ ID NO: 4:

( i ) SEQUENCE CHARACTERISTICS:
( A ) LENGTH: 28 amino acids
( B ) TYPE: Amino acid
( C ) STRANDEDNESS:
( D ) TOPOLOGY: Unknown ( x i ) SEQUENCE DESCRIPTION:SEQ ID NO: 4:

Cys Arg Ile Lys Gln Ile Ile Asn Met Trp Gln Glu Val Gly Lys
1 5 10 15

Ala Met Tyr Ala Pro Pro Ile Gly Gly Gln Ile Ser Cys
20 25

( 2 ) INFORMATION FOR SEQ ID NO: 5:

( i ) SEQUENCE CHARACTERISTICS:
( A ) LENGTH: 28 amino acids
( B ) TYPE: Amino acid
( C ) STRANDEDNESS:
( D ) TOPOLOGY: Unknown ( x i ) SEQUENCE DESCRIPTION:SEQ ID NO: 5:

Cys Arg Ile Lys Gln Ile Ile Asn Met Trp Gln Gly Val Gly Lys
1 5 10 15

Ala Met Tyr Ala Pro Pro Ile Gln Gly Gln Ile Arg Cys
20 25

( 2 ) INFORMATION FOR SEQ ID NO: 6:

( i ) SEQUENCE CHARACTERISTICS:
( A ) LENGTH: 28 amino acids
( B ) TYPE: Amino acid
( C ) STRANDEDNESS:
( D ) TOPOLOGY: Unknown ( x i ) SEQUENCE DESCRIPTION:SEQ ID NO: 6:

Cys Arg Ile Lys Gln Ile Ile Asn Met Trp Gln Glu Val Gly Lys
1 5 10 15

Ala Ile Tyr Ala Pro Pro Ile Ser Gly Gln Ile Arg Cys
20 25

( 2 ) INFORMATION FOR SEQ ID NO: 7:

( i ) SEQUENCE CHARACTERISTICS:
( A ) LENGTH: 28 amino acids
( B ) TYPE: Amino acid
( C ) STRANDEDNESS:
( D ) TOPOLOGY: Unknown ( x i ) SEQUENCE DESCRIPTION:SEQ ID NO: 7:

Cys Arg Ile Lys Gln Ile Val Asn Met Trp Gln Glu Val Gly Lys
1 5 10 15

Ala Met Tyr Ala Pro Pro Ile Ser Gly Gln Ile Lys Cys
20 25

( 2 ) INFORMATION FOR SEQ ID NO: 8:

( i ) SEQUENCE CHARACTERISTICS:

-continued ( A ) LENGTH: 28 amino acids
( B ) TYPE: Amino acid
( C ) STRANDEDNESS:
( D ) TOPOLOGY: Unknown ( x i ) SEQUENCE DESCRIPTION:SEQ ID NO: 8:

Cys Arg Ile Lys Gln Ile Ile Asn Met Trp Gln Lys Thr Gly Lys
1 5 10 15

Ala Met Tyr Ala Pro Pro Ile Ala Gly Val Ile Asn Cys
20 25

( 2 ) INFORMATION FOR SEQ ID NO: 9:

( i ) SEQUENCE CHARACTERISTICS:
( A ) LENGTH: 28 amino acids
( B ) TYPE: Amino acid
( C ) STRANDEDNESS:
( D ) TOPOLOGY: Unknown ( x i ) SEQUENCE DESCRIPTION:SEQ ID NO: 9:

Cys His Ile Lys Gln Ile Ile Asn Thr Trp His Lys Val Gly Arg
1 5 10 15

Asn Val Tyr Leu Pro Pro Arg Glu Gly Glu Leu Ser Cys
20 25

( 2 ) INFORMATION FOR SEQ ID NO: 10:

( i ) SEQUENCE CHARACTERISTICS:
( A ) LENGTH: 28 amino acids
( B ) TYPE: Amino acid
( C ) STRANDEDNESS:
( D ) TOPOLOGY: Unknown ( x i ) SEQUENCE DESCRIPTION:SEQ ID NO: 10:

Cys His Ile Arg Gln Ile Ile Asn Thr Trp His Lys Val Gly Lys
1 5 10 15

Asn Val Tyr Leu Pro Pro Arg Glu Gly Asp Leu Thr Cys
20 25

( 2 ) INFORMATION FOR SEQ ID NO: 11:

( i ) SEQUENCE CHARACTERISTICS:
( A ) LENGTH: 33 amino acids
( B ) TYPE: Amino acids
( C ) STRANDEDNESS:
( D ) TOPOLOGY: Unknown ( x i ) SEQUENCE DESCRIPTION:SEQ ID NO: 11:

Gln Ser Val Glu Ile Asn Cys Thr Arg Pro Asn Asn Asn Thr Arg
1 5 10 15

Lys Ser Ile Arg Ile Gln Arg Gly Pro Gly Arg Ala Phe Val Thr
20 25 30

Ile Gly Lys ( 2 ) INFORMATION FOR SEQ ID NO: 12:

( i ) SEQUENCE CHARACTERISTICS:
( A ) LENGTH: 33 amino acids
( B ) TYPE: Amino acid
( C ) STRANDEDNESS:
( D ) TOPOLOGY: Unknown ( x i ) SEQUENCE DESCRIPTION:SEQ ID NO: 12:

Thr Ser Val Glu Ile Asn Cys Thr Arg Pro Asn Asn Asn Thr Arg
1 5 10 15

Lys Arg Ile Arg Ile Gln Arg Gly Pro Gly Arg Ala Phe Val Thr
20 25 30

Ile Gly Lys ( 2 ) INFORMATION FOR SEQ ID NO: 13:

( i ) SEQUENCE CHARACTERISTICS:
( A ) LENGTH: 33 amino acids
( B ) TYPE: Amino acid
( C ) STRANDEDNESS:
( D ) TOPOLOGY: Unknown ( x i ) SEQUENCE DESCRIPTION:SEQ ID NO: 13:

Glu Ser Val Ala Ile Asn Cys Thr Arg Pro Asn Asn Asn Thr Arg
1 5 10 15

Lys Ser Ile Arg Tyr Gln Arg Gly Pro Gly Arg Ala Phe His Thr
20 25 30

Thr Gly Arg ( 2 ) INFORMATION FOR SEQ ID NO: 14:

( i ) SEQUENCE CHARACTERISTICS:
( A ) LENGTH: 31 amino acids
( B ) TYPE: Amino acid
( C ) STRANDEDNESS:
( D ) TOPOLOGY: Unknown ( x i ) SEQUENCE DESCRIPTION:SEQ ID NO: 14:

Glu Ala Val Glu Ile Asn Cys Thr Arg Pro Asn Asn Asn Thr Thr
1 5 10 15

Arg Ser Ile His Ile Gly Pro Gly Arg Ala Phe Tyr Ala Thr Lys
20 25 30

Asp ( 2 ) INFORMATION FOR SEQ ID NO: 15:

( i ) SEQUENCE CHARACTERISTICS:
( A ) LENGTH: 31 amino acids
( B ) TYPE: Amino acid
( C ) STRANDEDNESS:
( D ) TOPOLOGY: Unknown ( x i ) SEQUENCE DESCRIPTION:SEQ ID NO: 15:

Glu Ser Val Glu Ile Asn Cys Thr Arg Pro Tyr Asn Asn Val Arg
1 5 10 15

Arg Ser Leu Ser Ile Gly Pro Gly Arg Ala Phe Arg Thr Arg Glu
20 25 30

Ile ( 2 ) INFORMATION FOR SEQ ID NO: 16:

( i ) SEQUENCE CHARACTERISTICS:
( A ) LENGTH: 31 amino acids
( B ) TYPE: Amino acid
( C ) STRANDEDNESS:
( D ) TOPOLOGY: Unknown ( x i ) SEQUENCE DESCRIPTION:SEQ ID NO: 16:

Glu Ser Val Gln Ile Asn Cys Thr Arg Pro Asn Tyr Asn Lys Arg
1 5 10 15

Lys Arg Ile His Ile Gly Pro Gly Arg Ala Phe Tyr Thr Thr Lys
20 25 30

Asn

-continued ( 2 ) INFORMATION FOR SEQ ID NO: 17:

( i ) SEQUENCE CHARACTERISTICS:
( A ) LENGTH: 31 amino acids
( B ) TYPE: Amino acid
( C ) STRANDEDNESS:
( D ) TOPOLOGY: Unknown ( x i ) SEQUENCE DESCRIPTION:SEQ ID NO: 17:

Lys Ser Val Glu Ile Asn Cys Thr Arg Pro Asn Asn Asn Thr Lys
1 5 10 15

Lys Gly Ile Ala Ile Gly Pro Gly Arg Thr Leu Tyr Ala Arg Glu
20 25 30

Lys ( 2 ) INFORMATION FOR SEQ ID NO: 18:

( i ) SEQUENCE CHARACTERISTICS:
( A ) LENGTH: 31 amino acids
( B ) TYPE: Amino acid
( C ) STRANDEDNESS:
( D ) TOPOLOGY: Unknown ( x i ) SEQUENCE DESCRIPTION:SEQ ID NO: 18:

Ala Ser Val Gln Ile Asn Cys Thr Arg Pro Asn Asn Asn Thr Arg
1 5 10 15

Lys Ser Ile Thr Lys Gly Pro Gly Arg Val Ile Tyr Ala Thr Gly
20 25 30

Gln ( 2 ) INFORMATION FOR SEQ ID NO: 19:

( i ) SEQUENCE CHARACTERISTICS:
( A ) LENGTH: 31 amino acids
( B ) TYPE: Amino acid
( C ) STRANDEDNESS:
( D ) TOPOLOGY: Unknown ( x i ) SEQUENCE DESCRIPTION:SEQ ID NO: 19:

Glu Thr Val Thr Ile Asn Cys Thr Arg Pro Gly Asn Asn Thr Arg
1 5 10 15

Arg Gly Ile His Phe Gly Pro Gly Gln Ala Leu Tyr Thr Thr Gly
20 25 30

Ile ( 2 ) INFORMATION FOR SEQ ID NO: 20:

( i ) SEQUENCE CHARACTERISTICS:
( A ) LENGTH: 33 amino acids
( B ) TYPE: Amino acid
( C ) STRANDEDNESS:
( D ) TOPOLOGY: Unknown ( x i ) SEQUENCE DESCRIPTION:SEQ ID NO: 20:

Tyr Asn Leu Ser Cys His Cys Lys Arg Pro Gly Asn Lys Ile Val
1 5 10 15

Lys Gln Ile Met Leu Met Ser Gly Gly His Arg Val Phe His Ser
20 25 30

His Tyr Gln ( 2 ) INFORMATION FOR SEQ ID NO: 21:

-continued ( i ) SEQUENCE CHARACTERISTICS:
( A ) LENGTH: 30 amino acids
( B ) TYPE: Amino acid
( C ) STRANDEDNESS:
( D ) TOPOLOGY: Unknown ( x i ) SEQUENCE DESCRIPTION:SEQ ID NO: 21:

Tyr Asn Leu Thr Met Lys Cys Arg Arg Pro Gly Asn Lys Thr Val
1 5 10 15

Leu Pro Val Thr Ile Met Ser Leu Val Phe His Ser Gln Pro Val
20 25 30

( 2 ) INFORMATION FOR SEQ ID NO: 22:

( i ) SEQUENCE CHARACTERISTICS:
( A ) LENGTH: 4 amino acids
( B ) TYPE: Amino acid
( C ) STRANDEDNESS:
( D ) TOPOLOGY: Unknown ( x i ) SEQUENCE DESCRIPTION:SEQ ID NO: 22:

Gly Pro Gly Arg
1

( 2 ) INFORMATION FOR SEQ ID NO: 23:

( i ) SEQUENCE CHARACTERISTICS:
( A ) LENGTH: 13 amino acids
( B ) TYPE: Amino acid
( C ) STRANDEDNESS:
( D ) TOPOLOGY: Unknown ( x i ) SEQUENCE DESCRIPTION:SEQ ID NO: 23:

Gln Ser Val Glu Ile Asn Cys Thr Arg Pro Asn Asn Asn
1 5 10

( 2 ) INFORMATION FOR SEQ ID NO: 24:

( i ) SEQUENCE CHARACTERISTICS:
( A ) LENGTH: 6 amino acids
( B ) TYPE: Amino acid
( C ) STRANDEDNESS:
( D ) TOPOLOGY: Unknown ( x i ) SEQUENCE DESCRIPTION:SEQ ID NO: 24:

Gln Ser Val Glu Ile Asn
1 5

( 2 ) INFORMATION FOR SEQ ID NO: 25:

( i ) SEQUENCE CHARACTERISTICS:
( A ) LENGTH: 13 amino acids
( B ) TYPE: Amino acids
( C ) STRANDEDNESS:
( D ) TOPOLOGY: Unknown ( x i ) SEQUENCE DESCRIPTION:SEQ ID NO: 25:

Thr Arg Lys Ser Ile Arg Ile Gln Arg Gly Pro Gly Arg
1 5 10

( 2 ) INFORMATION FOR SEQ ID NO: 26:

( i ) SEQUENCE CHARACTERISTICS:
( A ) LENGTH: 20 amino acids
( B ) TYPE: Amino acids
( C ) STRANDEDNESS:
( D ) TOPOLOGY: Unknown -continued ( x i ) SEQUENCE DESCRIPTION:SEQ ID NO: 26:

Cys Thr Arg Pro Asn Asn Asn Thr Arg Lys Ser Ile Arg Ile Gln
1 5 10 15

Arg Gly Pro Gly Arg
20

( 2 ) INFORMATION FOR SEQ ID NO: 27:

( i ) SEQUENCE CHARACTERISTICS:
( A ) LENGTH: 15 amino acids
( B ) TYPE: Amino acids
( C ) STRANDEDNESS:
( D ) TOPOLOGY: Unknown ( x i ) SEQUENCE DESCRIPTION:SEQ ID NO: 27:

Arg Ile Gln Arg Gly Pro Gly Arg Ala Phe Val Thr Ile Gly Lys
1 5 10 15

( 2 ) INFORMATION FOR SEQ ID NO: 28:

( i ) SEQUENCE CHARACTERISTICS:
( A ) LENGTH: 20 amino acids
( B ) TYPE: Amino acids
( C ) STRANDEDNESS:
( D ) TOPOLOGY: Unknown ( x i ) SEQUENCE DESCRIPTION:SEQ ID NO: 28:

Thr Arg Lys Ser Ile Arg Ile Gln Arg Gly Pro Gly Arg Ala Phe
1 5 10 15

Val Thr Ile Gly Lys
20

( 2 ) INFORMATION FOR SEQ ID NO: 29:

( i ) SEQUENCE CHARACTERISTICS:
( A ) LENGTH: 13 amino acids
( B ) TYPE: Amino acids
( C ) STRANDEDNESS:
( D ) TOPOLOGY: Unknown ( x i ) SEQUENCE DESCRIPTION:SEQ ID NO: 29:

Cys Thr Arg Pro Asn Asn Asn Thr Arg Lys Ser Ile Arg
1 5 10

( 2 ) INFORMATION FOR SEQ ID NO: 30:

( i ) SEQUENCE CHARACTERISTICS:
( A ) LENGTH: 12 amino acids
( B ) TYPE: Amino acids
( C ) STRANDEDNESS:
( D ) TOPOLOGY: Unknown ( x i ) SEQUENCE DESCRIPTION:SEQ ID NO: 30:

Arg Gly Pro Gly Arg Ala Phe Val Thr Ile Gly Lys
1 5 10

( 2 ) INFORMATION FOR SEQ ID NO: 31:

( i ) SEQUENCE CHARACTERISTICS:
( A ) LENGTH: 24 amino acids
( B ) TYPE: Amino acids
( C ) STRANDEDNESS:
( D ) TOPOLOGY: Unknown ( x i ) SEQUENCE DESCRIPTION:SEQ ID NO: 31:

Val Lys Ile Glu Pro Leu Gly Val Ala Pro Thr Lys Ala Lys Arg
1 5 10 15

Arg Val Val Gln Arg Glu Lys Arg Ala
20

( 2 ) INFORMATION FOR SEQ ID NO: 32:

( i ) SEQUENCE CHARACTERISTICS:
( A ) LENGTH: 8 amino acids
( B ) TYPE: Amino acids
( C ) STRANDEDNESS:
( D ) TOPOLOGY: Unknown ( x i ) SEQUENCE DESCRIPTION:SEQ ID NO: 32:

Ala Ser Thr Thr Thr Asn Tyr Thr
1 5

( 2 ) INFORMATION FOR SEQ ID NO: 33:

( i ) SEQUENCE CHARACTERISTICS:
( A ) LENGTH: 15 amino acids
( B ) TYPE: Amino acids
( C ) STRANDEDNESS:
( D ) TOPOLOGY: Unknown ( x i ) SEQUENCE DESCRIPTION:SEQ ID NO: 33:

Ala Pro Thr Lys Ala Lys Arg Arg Val Val Gln Arg Glu Lys Arg
1 5 10 15

( 2 ) INFORMATION FOR SEQ ID NO: 34:

( i ) SEQUENCE CHARACTERISTICS:
( A ) LENGTH: 31 amino acids
( B ) TYPE: Amino acids
( C ) STRANDEDNESS:
( D ) TOPOLOGY: Unknown ( x i ) SEQUENCE DESCRIPTION:SEQ ID NO: 34:

Val Ala Pro Thr Lys Ala Lys Arg Arg Val Val Gln Arg Glu Lys
1 5 10 15

Arg Ala Val Gly Ile Gly Ala Leu Phe Leu Gly Phe Leu Gly Ala
20 25 30

Gly ( 2 ) INFORMATION FOR SEQ ID NO: 35:

( i ) SEQUENCE CHARACTERISTICS:
( A ) LENGTH: 16 amino acids
( B ) TYPE: Amino acids
( C ) STRANDEDNESS:
( D ) TOPOLOGY: Unknown ( x i ) SEQUENCE DESCRIPTION:SEQ ID NO: 35:

Lys Gln Ile Ile Asn Met Trp Gln Glu Val Gly Lys Ala Met Tyr
1 5 10 15

Ala ( 2 ) INFORMATION FOR SEQ ID NO: 36:

( i ) SEQUENCE CHARACTERISTICS:
( A ) LENGTH: 13 amino acids
( B ) TYPE: Amino acids
( C ) STRANDEDNESS:
( D ) TOPOLOGY: Unknown ( x i ) SEQUENCE DESCRIPTION:SEQ ID NO: 36:

His Glu Asp Ile Ile Ser Leu Trp Asn Gln Ser Ile Lys
1 5 10

-continued ( 2 ) INFORMATION FOR SEQ ID NO: 37:

( i ) SEQUENCE CHARACTERISTICS:
( A ) LENGTH: 30 amino acids
( B ) TYPE: Amino acids
( C ) STRANDEDNESS:
( D ) TOPOLOGY: Unknown ( x i ) SEQUENCE DESCRIPTION:SEQ ID NO: 37:

```
Arg Pro Gly Gly Gly Asp Met Arg Asp Asn Trp Arg Ser Glu Leu
1               5                   10                  15

Tyr Lys Tyr Lys Val Val Lys Ile Glu Pro Leu Gly Val Ala Pro
20                  25                  30
```

( 2 ) INFORMATION FOR SEQ ID NO: 38:

( i ) SEQUENCE CHARACTERISTICS:
( A ) LENGTH: 34 amino acids
( B ) TYPE: Amino acid
( C ) STRANDEDNESS:
( D ) TOPOLOGY: Unknown ( x i ) SEQUENCE DESCRIPTION:SEQ ID NO: 38:

```
Glu Ser Val Gln Ile Asn Cys Thr Arg Pro Asn Tyr Asn Lys Arg
1               5                   10                  15

Lys Arg Ile His Ile Gly Pro Gly Arg Ala Phe Tyr Thr Thr Lys
20                  25                  30

Asn Ile Ile Gly
```